United States Patent
Yang et al.

(10) Patent No.: US 9,663,611 B2
(45) Date of Patent: May 30, 2017

(54) CONJUGATED POLYMERS FOR ELECTRONIC DEVICES

(71) Applicant: The Regents of the University of California, Oakland, CA (US)

(72) Inventors: Yang Yang, Los Angeles, CA (US); Letian Dou, Los Angeles, CA (US); Wei-Hsuan Chang, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/338,599

(22) Filed: Jul. 23, 2014

(65) Prior Publication Data

US 2015/0028265 A1    Jan. 29, 2015

Related U.S. Application Data

(60) Provisional application No. 61/857,578, filed on Jul. 23, 2013.

(51) Int. Cl.
| | | |
|---|---|---|
| *C08G 61/12* | (2006.01) | |
| *C07D 487/04* | (2006.01) | |
| *H01L 51/00* | (2006.01) | |
| *H01L 51/42* | (2006.01) | |

(52) U.S. Cl.
CPC ......... *C08G 61/124* (2013.01); *C07D 487/04* (2013.01); *C08G 61/126* (2013.01); *H01L 51/0036* (2013.01); *H01L 51/0043* (2013.01); *H01L 51/0094* (2013.01); *C08G 2261/12* (2013.01); *C08G 2261/18* (2013.01); *C08G 2261/3223* (2013.01); *C08G 2261/3225* (2013.01); *C08G 2261/3241* (2013.01); *C08G 2261/344* (2013.01); *C08G 2261/91* (2013.01); *H01L 51/0053* (2013.01); *H01L 51/4253* (2013.01); *Y02E 10/549* (2013.01)

(58) Field of Classification Search
CPC  C08G 61/124; C08G 61/126; C08G 2261/18; C08G 2261/91; H01L 31/0256
USPC .......... 252/511, 506, 510; 548/453; 526/240
See application file for complete search history.

(56) References Cited

U.S. PATENT DOCUMENTS

| | | | | |
|---|---|---|---|---|
| 2010/0041177 A1* | 2/2010 | Yang | ................... | H01L 51/0008 438/82 |
| 2012/0168728 A1* | 7/2012 | Hawker | ................. | B82Y 30/00 257/40 |
| 2012/0186652 A1* | 7/2012 | Pan | ........................ | B82Y 10/00 136/263 |
| 2014/0243488 A1* | 8/2014 | Sato | ..................... | C08G 61/123 526/118 |

FOREIGN PATENT DOCUMENTS

WO    WO 2015042609 A1 *  3/2015  ......... H01L 51/4253

OTHER PUBLICATIONS

Munazza Shahid et al., "Low band gap selenophene-diketopyrrolopyrrole polymers exhibiting high and balanced ambipolar performance in bottom-gate transistors", Chemical Science, 2012, 3, 181-185, published on-line Sep. 1, 2011.*
Letian Dou et al., "A Selenium-Substituted Low-Bandgap Polymer iwth Versatile Photovoltaic Applications", Advanced Materials, 2013, 25, 825-831, published on-line Nov. 2, 2012.*
Amb et al., "Dithienogermole As a Fused Electron Donor in Bulk Heterojunction Solar Cells," Journal of the American Chemical Society 2011, 133, 10062-65.
Bailey-Salzman et al., "Semitransparent Organic Photovoltaic Cells," Applied Physics Letters 2006, 88, 233502.
Ballantyne et al., "Studies of Highly Regioregular Poly(3-hexylselenophene) for Photovoltaic Applications," Advanced Materials 2007, 19, 4544-47.
Beaujuge et al., "Molecular Design and Ordering Effects in Functional Materials for Transistor and Solar Cell Applications," Journal of the American Chemical Society 2011, 133, 20009-20029.
Bijleveld et al., "Poly(diketopyrrolopyrrole?terthiophene) for Ambipolar Logic and Photovoltaics," Journal of the American Chemical Societ, 2009, vol. 131, p. 16616-16617.
Boudreault et al., "Processable Low-Bandgap Polymers for Photovoltaic Applications," Chemistry of Materials 2011, 23, 456-469.
Brabec et al., "Plastic Solar Cells," Advanced Functional Materials 2011, 11, 15.
Burdick et al., "Spectral Response and I-V Measurements of Tandem Amorphous-Silicon Alloy Solar Cells ," Solar Cells 1986, 18, 301-314.
Chen et al., "Polyalkylthiophenes with the Smallest Bandgap and the Highest Intrinsic Conductivity," Synthetic Meals 1993, (60), 175-177.
Chen et al., "Polymer Solar Cells with Enhanced Open-Circuit Voltage and Efficiency," Nature Photonics 2009, 3, 649-653.

(Continued)

*Primary Examiner* — Douglas McGinty
(74) *Attorney, Agent, or Firm* — Venable LLP; Henry J. Daley; Annette K. Kwok

(57) ABSTRACT

A conjugated polymer for electronic devices can include a repeated unit having the structure of formula (I)

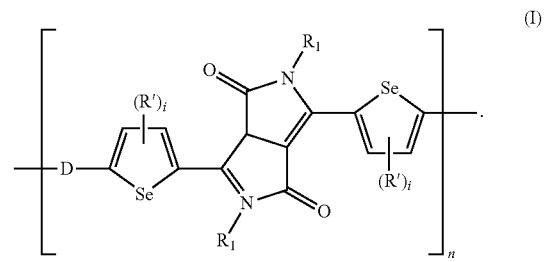

17 Claims, 14 Drawing Sheets

(56) References Cited

OTHER PUBLICATIONS

Chen et al., "Visibly Transparent Polymer Solar Cells Produced by Solution Processing," ACS Nano 2012, 6, 7185-7190.

Cheng et al., "Synthesis of Conjugated Polymers for Organic Solar Cell Applications," Chemical Review 2009, 109, 5868-5923.

Chou et al., "Metal-Oxide Interconnection Layer for Polymer Tandem Solar Cells with an Inverted Architecture," Advanced Materials 2010, 23, 1282-1286.

Chu et al., "Bulk Heterojunction Solar Cells Using Thieno[3,4-c]pyrrole-4,6-dione and Dithieno[3,2-b:2',3'-d]silole Copolymer with a Power Conversion Efficiency of 7.3%," Journal of the American Chemical Society, 2011, 133, 4250-4253.

Dennler et al., "Design Rules for Donors in Bulk-Heterojunction Tandem Solar Cells Towards 15% Energy-Conversion Efficiency," Advanced Materials, 2008, vol. 20, 579-583.

Dou et al., "A Selenium-substituted Low-Bandgap Polymer with Versatile Photovoltaic Applications," Advanced Materials 2013, 25, 825-831.

Dou et al., "Systematic Investigation of Benzodithiophene- and Diketopyrrolopyrrole-Based Low-Bandgap Polymers Designed for Single Junction and Tandem Polymer Solar Cells," Journal of the American Chemical Society, 2012, 134, 1007110079.

Dou et al., "Tandem Polymer Solar Cells Featuring a Spectrally Matched Low-Bandgap Polymer," Nature Photonics 2012, 6, 180-185.

Gaynor et al., "Fully Solution-Processed Inverted Polymer Solar Cells with Laminated Nanowire Electrodes," ACS Nano 2010, 4, 30-34.

Gevaerts et al., "Solution Processed Polymer Tandem Solar Cell Using Efficient Small and Wide bandgap Polymer:Fullerene Blends," Advanced Materials 2012, 24, 2130-2134.

Ha et al., "2,5-Bis(2-octyldodecyl)pyrrolo[3,4-c]pyrrole-1,4-(2H,5H)-dione-Based Donor-Acceptor Alternating Copolymer Bearing 5,5?-Di(thiophen-2-yl)-2,2?-biselenophene Exhibiting 1.5 cm2•V-1•s-1 Hole Mobility in Thin-Film Transistors," Journal of the American Chemical Society 2011, 133, 10364-10367.

Hadipour et al., "Solution-Processed Organic Tandem Solar Cells," Advanced Functional Materials 2006, 16, 1897-1903.

He et al., "Indene C60 Bisadduct: A New Acceptor for High-Performance Polymer Solar Cells," Journal of the American Chemical Society 2010, 132, 1377-1382.

He et al., "Simultaneous Enhancement of Open-Circuit Voltage, Short-Circuit Current Density, and Fill Factor in Polymer Solar Cells," Advanced Materials 2011, 23, 4636-4643.

Hou et al., "Synthesis, Characterization, and Photovoltaic Properties of a Low Band Gap Polymer Based on Silole-Containing Polythiophenes and 2,1,3-Benzothiadiazole," Journal of the American Chemical Society 2008, 130, 16144-45.

Huang et al., "A Semi-Transparent Plastic Solar Cell Fabricated by a Lamination Process," Advanced Materials 2008, 20, 415-419.

Huo et al., "A Polybenzo[1,2-b:4,5-b?]dithiophene Derivative with Deep HOMO Level and Its Application in High-Performance Polymer Solar Cells," Angewandte Chemie Int. Ed., 2010, vol. 49, p. 1500-1503.

Huo et al., "Bandgap and Molecular Level Control of the Low-Bandgap Polymers Based on 3,6-Dithiophen-2-yl-2,5-dihydropyrrolo[3,4-c]pyrrole-1,4-dione toward Highly Efficient Polymer Solar Cells," Macromolecules 2009, 42, 6564-71.

Huo et al., "Replacing Alkoxy Groups with Alkylthienyl Groups: A Feasible Approach to Improve the Properties of Photovoltaic Polymers," Angewandte Chemie Int. Ed. 2011, 123, 9871-76.

Iraqi et al., "Synthesis and characterisation of telechelic regioregular head-to-tail poly(3-alkylthiophenes), " Journal of Materials Chemistry 1998, (8) 25-29.

Kim et al., "Efficient Tandem Polymer Solar Cells Fabricated by All-Solution Processing," Science 2007, 317, 222-225.

Klein, et al. "Poly(3-hexylselenophene) solar cells: Correlating the optoelectronic device performance and nanomorphology imaged by low-energy scanning Transmission electron microscopy," Journal of Polymer Science. Part B: Polymer Physics 2012, 50, 198-206.

Krebs, "Fabrication and processing of polymer solar cells: A review of printing and coating techniques," Solar Energy Materials and Solar Cells 2009, 93, 394-412.

Kronemeijier et al., "A Selenophene-Based Low-Bandgap Donor-Acceptor Polymer Leading to Fast Ambipolar Logic," Advanced Materials 2012, 24, 1558-1565.

Li et al., "Efficient Inverted Polymer Solar Cells," Applied Physics Letters 2006, 88, 253503.

Li et al., "Enhancing the Photocurrent in Diketopyrrolopyrrole-Based Polymer Solar Cells via Energy Level Control," Journal of the American Chemical Society, 2012, 134, 13787-13795.

Liang et al., "For the Bright Future—Bulk Heterojuntion Polymer Solar Cells with Power Conversion Efficiency of 7.4%," Advanced Materials 2010, 22, E135-138.

Li et al., "High-efficiency solution processable polymer photovoltaic cells by self-organization of polymer blends," Nature Materials 2005, 4, 864.

Li et al., "Polymer Solar Cells," Nature Photonics 2012, 6, 153.

Loewe et al., "Regioregular, Head-to-Tail Coupled Poly(3-alkylthiophenes) Made Easy by the GRIM Method: Investigation of the Reaction and the Origin of Regioselectivity," Macromolecules, 2001, (34), 4324-4333.

McCollough et al., "Enhanced electrical conductivity in regioselectively synthesized poly(3-alkylthiophenes)," Journal of the Chemical Society, Chemical Communications 1992, 70.

Meiss et al., "Near-Infrared Absorbing Semitransparent Organic Solar Cells," Applied Physics Letters 2011, 99, 193307.

Meusel et al., "Spectral Response Measurements of Monolithic GaInP/Ga(In)As/Ge Triple-Junction Solar Cells: Measurement Artifacts and Their Explanation," Progress in Photovoltaics Research 2003, 11, 499-514.

Miyaura et al., "Palladium-Catalyzed Cross-Coupling Reactions of Organoboron Compounds," Chemical Reviews 1995 (95): 2457-2483.

Ng et al., "Optical Enhancement in Semitransparent Polymer Photovoltaic Cells," Applied Physics Letters 2007, 90, 103505.

Peet et al., "Efficiency Enhancement in Low-Bandgap Polymer Solar Cells by Processing with Alkane Dithiols," Nature Materials 2007, 6, 497-500.

Saadeh et al., "Polyselenopheno[3,4-b]selenophene for Highly Efficient Bulk Heterojunction Solar Cells," ACS Macro Letters 2012, 1, 361-365.

Scharber et al., "Design Rules for Donors in Bulk-Heterojunction Solar Cells-Towards 10 Energy-Conversion Efficiency," Advanced Materials, 2006, vol. 18, p. 789-794.

Shahid et al, "Low Band Gap Selenophene-Diketopyrrolopyrrole Polymers Exhibiting High and Balanced Ambipolar Performance in Bottom-Gate Transistors" Chemical Science 2012, 3, 181-185.

Shahid et al., "Photovoltaic and Field Effect Transitor Performance of Selenophene and Thiophene Diketopyrrolopyrrole Co-Polymers with Dithienothiophene," Journal of Materials Chemistry 2012, 22, 12817-12823.

Shockley et al., "Detailed Balance Limit of Efficiency of p-n Junction Solar Cells," Journal of Applied Physics 1961, 32, 510.

Sista et al., "Highly Efficient Tandem Polymer Photovoltaic Cells" Advanced Materials 2010, 22, 380-83.

Thompson et al., "Polymer-Fullerene Composite Solar Cells," Angewandte Chemie Int. Ed. 2008, 47, 58-77.

Woo et al., "Incorporation of Furan into Low Band-Gap Polymers for Efficient Solar Cells," Journal of the American Chemical Society 2010, 132, 15547-49.

Yang et al., "A Robust Inter-Connecting Layer for Achieving High Performance Tandem Polymer Solar Cells," Advanced Materials 2011, 23, 3465-3470.

Yu et al., "Polymer Photovoltiac Cells: Enhanced Efficiencies Via a Network of Internal Donor-Acceptor Heterojunctions," Science 1995, 270, 1789-91.

Zhou et al., "Diketopyrrolopyrrole-Based Semiconducting Polymer for Photovoltaic Device with Photocurrent Response Wavelengths up to 1.1 ?m," Macromolecules 2010, 43, 821-826.

\* cited by examiner

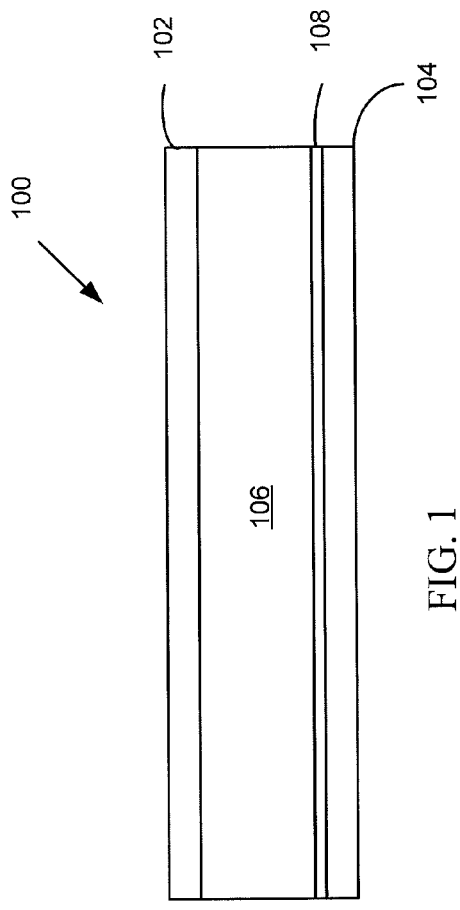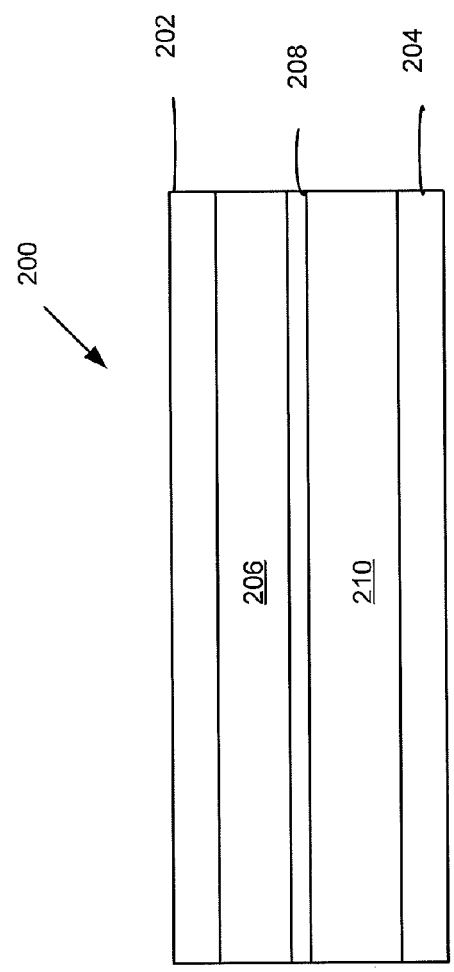

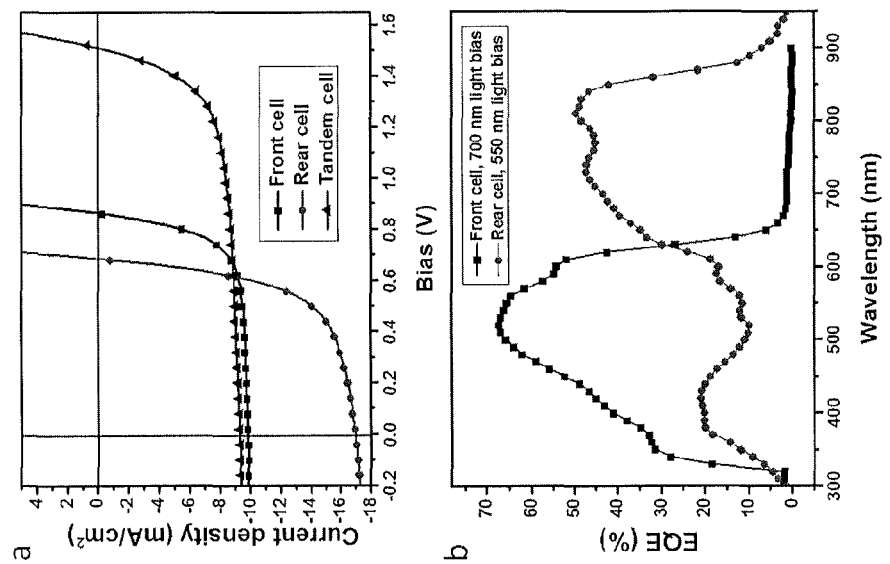
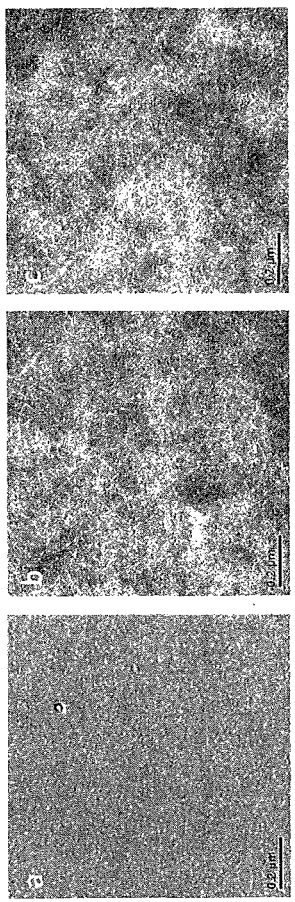
FIG. 13
FIG. 14

CONJUGATED POLYMERS FOR ELECTRONIC DEVICES

CLAIM OF PRIORITY

This application claims priority to provisional application No. 61/857,578, filed Jul. 23, 2013, which is incorporated by reference in its entirety.

STATEMENT OF GOVERNMENT SUPPORT

This invention was made with Government support under Grant No. FA9550-12-1-0074, awarded by the U.S. Air Force Office of Scientific Research. The Government has certain rights in this invention.

BACKGROUND

The present invention relates to conjugated polymers for electronic devices.

SUMMARY

In one aspect, a conjugated polymer includes a repeated unit having the structure of formula (I)

(I)

Each $R_1$ independently can be H, a halogen, optionally substituted alkyl, optionally substituted aryl, or optionally substituted heteroaryl. Each R' independently can be H, a halogen, optionally substituted alkyl, optionally substituted aryl, or optionally substituted heteroaryl. Each i, independently, can be 0, 1, or 2. D can be a donor moiety. n can be an integer.

In another aspect, a photovoltaic device includes a conjugated polymer having the structure of formula (I) as a photovoltaic material.

In another aspect, a method of making a conjugated polymer having the structure of formula (I) includes co-polymerizing a monomer having the structure of formula (II) and a monomer having the structure of formula (III):

X—D—X  (II)

(III)

In some embodiments, each X, independently, can be a boronic acid group, a boronic acid ester group, a magnesium halide group, a zinc halide group, or a trialkyl tin group; and each Y, independently, can be Cl, Br, I. In other embodiments, each X, independently, can be Cl, Br, or I; and each Y, independently, can be a boronic acid group, a boronic acid ester group, a magnesium halide group, a zinc halide group, or a trialkyl tin group.

In another aspect, a compound can have the structure of formula (III):

(III)

Each $R_1$ independently can H, a halogen, optionally substituted alkyl, optionally substituted aryl, or optionally substituted heteroaryl. Each R' independently can be H, a halogen, optionally substituted alkyl, optionally substituted aryl, or optionally substituted heteroaryl. Each i, independently, can be 0, 1, or 2. Each Y, independently, can be a boronic acid group, a boronic acid ester group, a magnesium halide group, a zinc halide group, a trialkyl tin group, Cl, Br, or I.

BRIEF DESCRIPTION OF THE DRAWINGS

FIG. 1 is a schematic illustration of an electro-optic device.

FIG. 2 is a schematic illustration of a tandem electro-optic device.

FIG. 13 shows TEM images of (a) PBDTT-FDPP:$PC_{71}BM$, (b) PBDTT-DPP:$PC_{71}BM$, and (c) PBDTT-SeDPP:$PC_{71}BM$ blend films processed in DCB.

FIG. 14 shows (a) Current density-voltage characteristics of the single junction front cell, single junction rear cell, and inverted tandem cell under AM1.5G illumination (100 mW/cm$^2$). (b) EQE of the P3HT:ICBA based front cell, PBDTT-SeDPP:PC$_{71}$BM based rear cell in a typical tandem device.

DETAILED DESCRIPTION

Figure 3B:
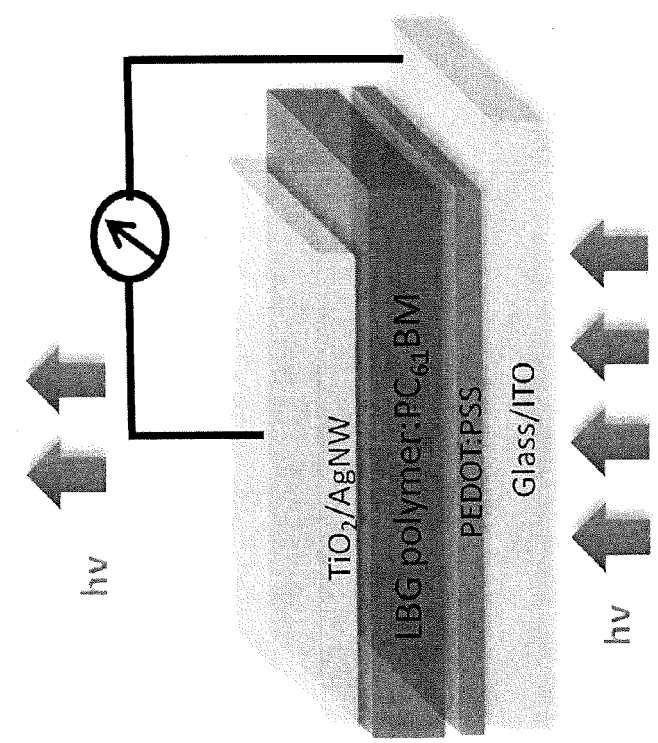
FIGS. 3A-3B are schematic illustrations of polymer solar cell devices.

The content of all references cited herein, including articles, published patent applications, and patents are hereby incorporated by reference.

Organic photovoltaic (OPV) devices provide an opportunity to utilize the solar energy efficiently while maintaining low cost. (Li, G.; Zhu, R.; Yang, Y. *Nat. Photon.* 2012, 6, 153) To harvest a greater part of the solar spectrum, lowering the energy bandgap of the active material is a major task for materials scientists. The design and synthesis of low-bandgap (LBG) conjugated polymers for use as electron donor materials for bulk heterojunction (BHJ) polymer solar cell (PSC) applications have attracted remarkable attention during the last decade. (Cheng, Y. J.; Yang, S. H.; Hsu, C. S. *Chem. Rev.* 2009, 109, 5868) The reasons for pursuing LBG polymers include: 1) The Shockley-Quiesser equation indicates a bandgap of around 1.4 eV is ideal for a single junction solar cell device. 2) Tandem PSCs require an active material with a bandgap less than 1.5 eV together with a wide bandgap (WBG) material having a bandgap around 1.9 eV. (Dou, L. T.; You, J. B.; Yang, J.; Chen, C.-C.; He, Y. J.; Murase, S.; Moriarty, T.; Emery, K.; Li, G.; Yang, Y. *Nat. Photon.* 2012, 6, 180) 3) Some specific applications such as visibly-transparent PSCs need an active material to be more absorbing of near-infrared (NIR) and ultra-violet (UV) light and less absorbing of visible light. (Chen, C.-C.; Dou, L. T.; Zhu, R.; Chung, C.-H.; Song, T.-B.; Zheng, Y. B.; Hawks, S.; Li, G.; Weiss, P. S.; Yang, Y. *ACS Nano* 2012, 6, 7185) In order to realize these goals, several synthetic strategies have been proven to be very effective in terms of narrowing the bandgap of organic polymeric materials. However, a small bandgap doesn't directly guarantee high power conversion efficiency (PCE) of the solar cell devices. Proper alignment of the highest occupied molecular orbital (HOMO) and lowest unoccupied molecular orbital (LUMO) energy levels are also critical for efficient charge transfer to the electron acceptor material (for example, [6,6]-phenyl-C$_{71}$-butyric acid methyl ester [PC$_{71}$BM]) and to ensure a large open circuit voltage (V$_{OC}$) of the device; High charge carrier mobility as well as favorable morphology when blended with the acceptor material are required as well to enhance device's short circuit current (J$_{SC}$) and fill factor (FF). So far, PCEs of over 7% for single junction devices have been achieved using carefully-designed active materials with bandgaps of 1.8 to 1.6 eV (mid-bandgap polymer, or MBG polymer). ((a) Chen, H. Y.; Hou, J. H.; Zhang, S. Q.; Liang, Y. Y.; Yang, G. W.; Yang, Y.; Yu, L. P.; Wu, Y.; Li, G. *Nat. Photon.* 2009, 3, 649-653. (b) Liang, Y. Y.; Xu, Z.; Xia, J.; Tsai, S. T.; Wu, Y.; Li, G.; Ray, C.; Yu, L. P. *Adv. Mater.* 2010, 22, E135) Regardless of great efforts having been made, there is still a lack of high performance polymers with bandgaps less than 1.5 eV that can compete with the state-of-art MBG polymers such as the thionothiophene (TT) and benzodithiophene (BDT) based PTB7 and PBDTTT-CF.

Recently, we have demonstrated a series of LBG polymers based on alternating diketopyrrolopyrrole (DPP) and thienylbenzodithiophene (BDTT) units. When the BDTT unit is copolymerized with the furan-containing DPP unit (FDPP), the resulting polymer (PBDTT-FDPP, Eg=1.51 eV) gives a PCE ~5% in a single junction solar cell. By switching the furan to a thiophene moiety, PBDTT-DPP (Eg=1.46 eV) shows increased J$_{SC}$ and FF, and this resulted in a higher PCE of 6.5%. The successful application of PBDTT-DPP in tandem PSCs has led to a National Renewable Energy Laboratory certified PCE of 8.6% and its application in visibly-transparent PSCs has led to ~4% PCE with over 60% transparency in the visible region. Nevertheless, the efficiencies were limited mainly by the relatively narrow absorption range (up to 850 nm) and low external quantum efficiency (EQE, <50%) in the NIR region. Further lowering the bandgap to harvest more photons in the NIR part of the solar radiation, as well as increasing the charge carrier mobility of the LBG polymers is desired to reach higher efficiency in both types of devices. Very recently, it has been found that changing the sulfur atom on the thiophene moiety of the DPP unit to a selenium atom to form the selenophene-based DPP (SeDPP) unit in the conjugated polymer backbone can decrease the bandgap and enhance the charge transport properties in organic field effect transistor (FET) devices. (Kronemeijier, A. J.; Gili, E.; Shahid, M.; Pivnay, J.; Salleo, A.; Heeney, M.; Sirringhaus, H. *Adv. Mater.* 2012, 24, 1558) However, the photovoltaic performance of the SeDPP-based LBG polymer (PSeDPPDTT) was lower than its thiophene counterpart mainly due to its higher HOMO level and thus lower Voc of the device. (Shahid, M.; Ashraf. R. S.; Huang, Z. G.; Kronemeijier, A. J.; Mccarthy-Ward, T.; McCulloch, I.; Durrant, J. R.; Sirringhaus, H.; Heeney, M. *J. Mater. Chem.* 2012, 22, 12817) On the other hand, Yu et al. recently reported a Se-substituted PTB8 polymer based on TT and BDT units, which showed similar V$_{OC}$, FF, higher J$_{SC}$, and thus higher PCE than its thiophene counterpart. (Saadeh, H. A.; Lu, L. Y.; He, F.; Bullock, J. E.; Wang, W.; Carsten, B.; Yu. L. P. *ACS Macro Lett.* 2012, 1, 361).

A selenium-substituted LBGpolymer with versatile photovoltaic applications is described in Dou, L.; Chang, W.-H.; Gao, J.; Chen, C.-C.; You, J.; and Yang, Y.; "A Selenium-substituted Low-Bandgap Polymer with Versatile Photovoltaic Applications," *Adv. Mat.* 2013, 25, 825-831, which is incorporated by reference in its entirety.

Conjugated polymers are polymers containing π-electron conjugated units along the main chain. These polymers can be used as active layer materials of different kinds of electronic devices, including electro-optic devices, such as polymer light emission devices, PSCs, polymer FETs. Conjugated polymers for solar cells should possess some typical properties, such as high mobility, strong sunlight harvesting, easy processability, and proper molecular energy level. Lots of conjugated polymers have proven to be good solar cell materials. For example, some derivatives of poly(p-phenylene vinylene), such as MEH-PPV and MDMO-PPV, and some derivatives of poly(3-alky-thiophene), such as P3HT and P3OT, and some conjugated polymers with heterocyclic aromatic rings, such as poly[2,6-(4,4-bis-(2-ethylhexyl)-4H-cyclopenta[2,1-b; 3,4-b']-dithiophene)-alt-4,7-(2,1,3-benzothiadiazole)] (PCPDTBT) and poly[4,8-bis-substituted-benzo[1,2-b:4,5-b']dithiophene-2,6-diyl-alt-4-substituted-thieno[3,4-b]thiophene-2,6-diyl] (PBDTTT), have been successfully used as photo-active layer materials. Although the PCE of the solar cell devices based on these polymers has reached nearly 7%, it is still much lower than that of inorganic semiconductor solar cells.

Therefore, there is a need for conjugated polymers that have desirable electronic and optical properties for use in electronic devices.

DEFINITIONS

The term "alkyl" used alone or as part of a larger moiety (i.e. "alkoxy," "hydroxyalkyl," "alkoxyalkyl," and "alkoxycarbonyl") includes both straight and branched chains containing one to twenty carbon atoms, as well as cyclic structures such as cyclopropyl and cyclobutyl. Examples of alkyl groups include methyl (Me), ethyl (Et), propyl (Pr) (including n-propyl (''Pr or n-Pr), isopropyl ($^i$Pr or i-Pr) and cyclopropyl ($^c$Pr or c-Pr)), butyl (Bu) (including n-butyl (''Bu or n-Bu), isobutyl ($^i$Bu or i-Bu), tert-butyl ($^t$Bu or t-Bu) and cyclobutyl ($^c$Bu or c-Bu)), pentyl (Pe) (including n-pentyl) and so forth. Alkyl groups also include mixed cyclic and linear alkyl groups, such as cyclopentylmethyl, cyclopentylethyl, cyclohexylmethyl, etc., so long as the total number of carbon atoms is not exceeded.

The term "aryl" used alone or as part of a larger moiety, refers to mono-, bi-, or tricyclic aromatic hydrocarbon ring systems having five to fourteen members, such as phenyl, 1-naphthyl, 2-naphthyl, 1-anthracyl and 2-anthracyl. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenanthridinyl or tetrahydronaphthyl, where the radical or point of attachment is on the aromatic ring. The term "aryl" used alone or as part of a larger moiety also refers to aryl rings that are substituted such as, for example, 4-chlorophenyl, 3,4-dibromophenyl and so forth. An aryl group may have more than one substituent, up to the total number of free substitution positions. For example, an aryl group may have 1, 2, 3, 4, or 5 substituents. The substituents may the same or different. Substituents on an aryl group include hydrogen, halogen, alkyl, alkenyl, nitro, hydroxyl, amino, alkylamino, alkoxy, and alkylthio, O-acyl, N-acyl, S-acyl as defined herein.

The term "heteroaryl", used alone or as part of a larger moiety, refers to heteroaromatic ring groups having five to fourteen members, preferably five to ten, in which one or more ring carbons, preferably one to four, are each replaced by a heteroatom such as N, O, or S. Examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 3-pyrazolyl, 4-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, or benzoisoxazolyl. Also included within the scope of the term "heteroaryl", as it is used herein, is a group in which a heteroaromatic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" may be used interchangeably with the term "heteroaryl ring" or the term "heteroaromatic."

The term "substituted" as in "substituted alkyl," "substituted aryl", "substituted heteroaryl" and the like, is meant that at least one hydrogen atom bound to a carbon (or other) atom is replaced with one or more non-hydrogen substituents. Such substituents include, but are not limited to, functional groups such as alkyl (as defined herein), halo (fluoro, chloro, bromo, or iodo), haloalkyl (alkyl, as defined herein, substituted with one or more F, Cl, Br, or I atoms, such as, for example, trifluoromethyl), hydroxyl, alkylthio, alkoxy, aryloxy, alkylcarbonyl, acyloxy, nitro, cyano, and the like.

Polymers

Conjugated polymers for PSC desirably have high mobility, thus the main chains of the conjugated polymers should have a planar structure according to some embodiments. In addition, the polymers desirably provide intermolecular interactions, such as π-π stacking which can facilitate charge transfer between two adjacent polymer chains. Some materials can have a low bandgap to provide strong harvesting of sunlight, and proper molecular energy levels that match with electrode and electron acceptor materials in PSC devices. It thus would be desirable according to some embodiments to provide conjugated polymers as photovoltaic materials that possess some or all of the properties mentioned above.

Described herein are polymers having a repeated unit of formula (I):

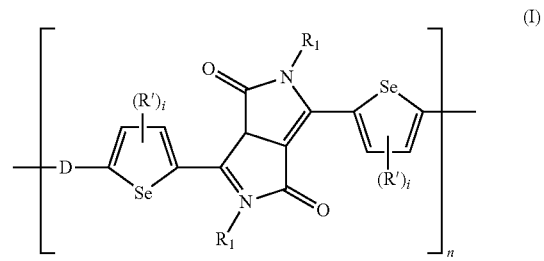

Each $R_1$ independently can be H, a halogen, optionally substituted alkyl, optionally substituted aryl, or optionally substituted heteroaryl. Each R' independently can be H, a halogen, optionally substituted alkyl, optionally substituted aryl, or optionally substituted heteroaryl. Each i, independently, can be 0, 1, or 2. D can be a donor moiety. n can be an integer.

The selenium-diketopyrrolopyrrole (SeDPP) unit in the polymer backbone can act as a strong acceptor in the polymer system. $R_1$ groups and/or R' groups can be selected so as to adjust the solubility and/or the electronic properties of the polymer.

D can be an electron-donating moiety that is selected to donate electrons to the acceptor. Typically D moieties possess relatively large HOMO energy level compared to that of acceptor moieties.

Examples of suitable D moieties include, but are not limited to, the following:

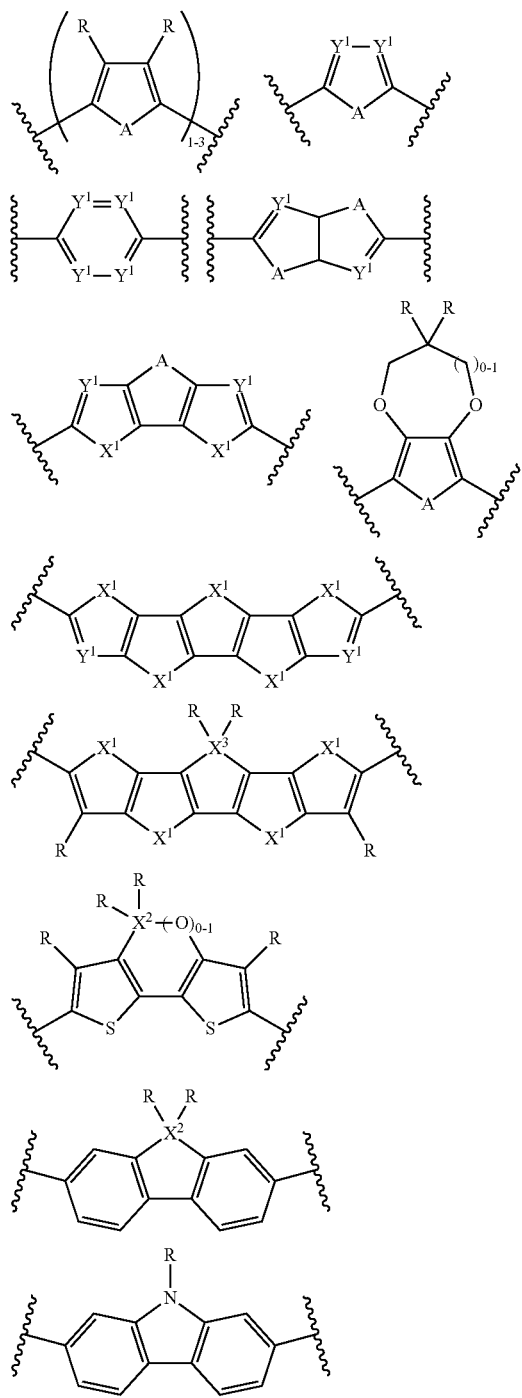

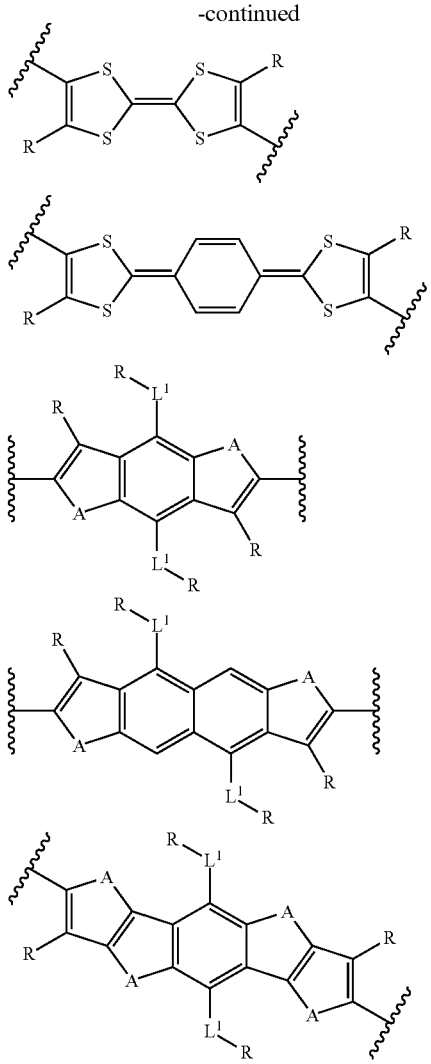

where each R independently can be H, a halogen, cyano, nitro, optionally substituted alkyl, optionally substituted aryl, or optionally substituted heteroaryl; each A, independently, can be O, S, or Se; each $Y^1$, independently, can be N or C—R; each $X^1$, independently, can be S or Se; each $X^2$, independently, can be C, Si, or Ge; each $X^3$, independently, can be Si or Ge; and each $L^1$, independently, can be a bond, O, S, optionally substituted arylene, or optionally substituted heteroarylene.

In the above structures, in some embodiments, R can be, for example, H, a halogen, $CF_3$, CN, $NO_2$, or an optionally substituted alkyl group with carbon atom number of 1-18. In some embodiments, each X is S and each R is optionally substituted alkyl.

Examples of suitable D moieties include, but are not limited to, the following:

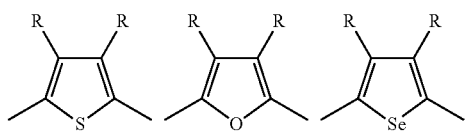

-continued
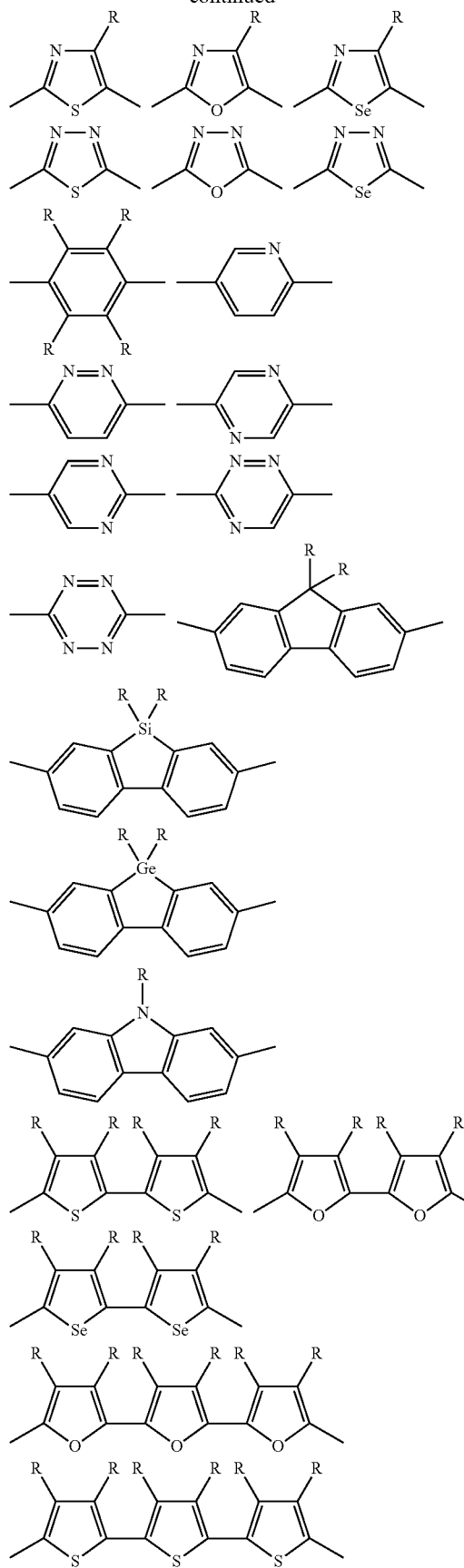
-continued
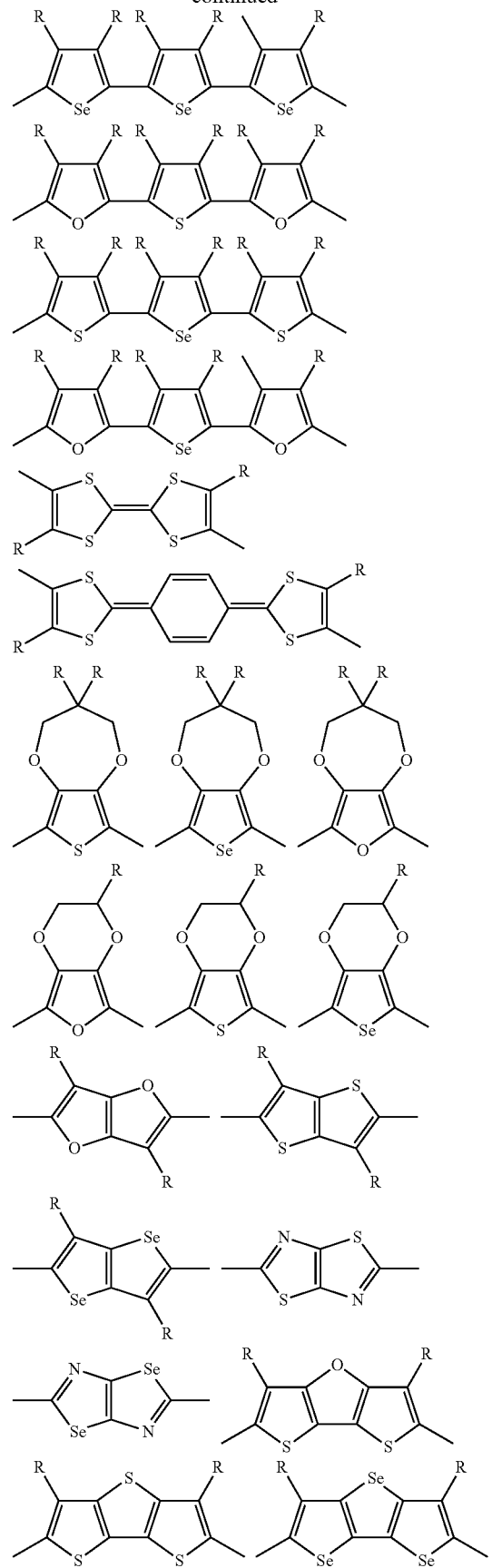

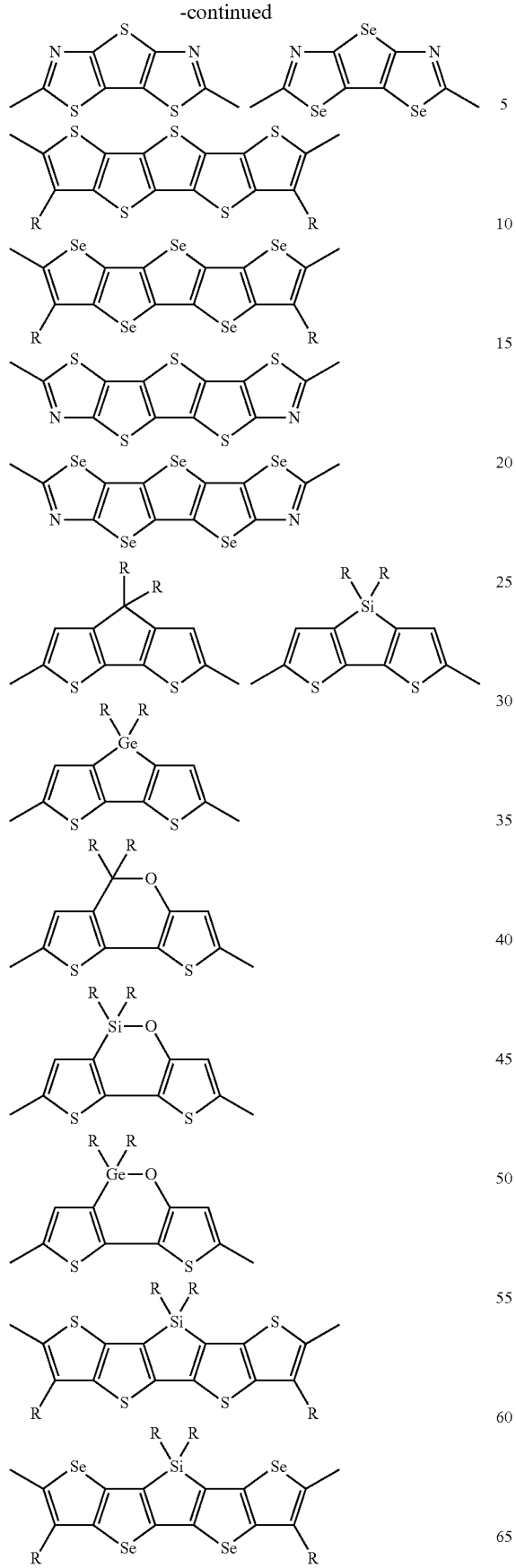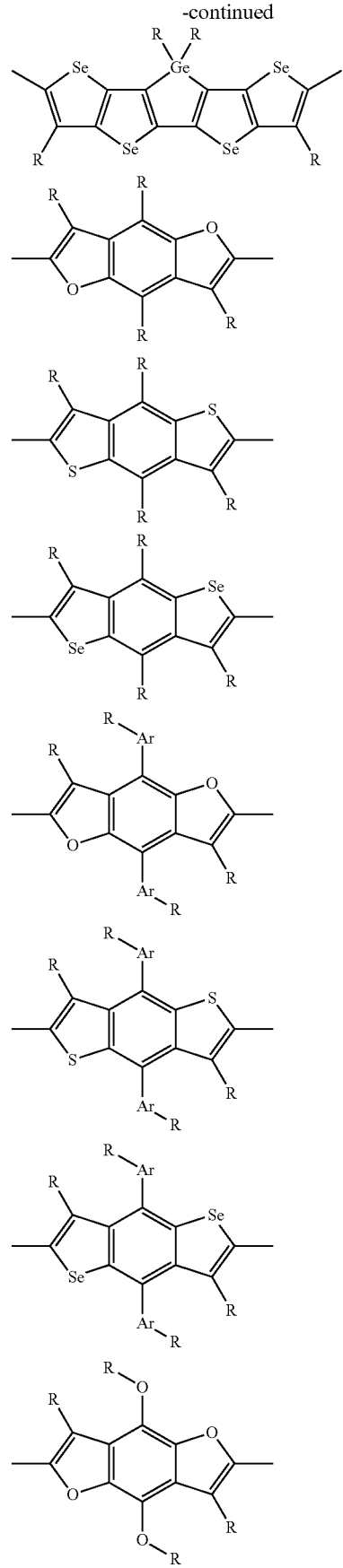

-continued

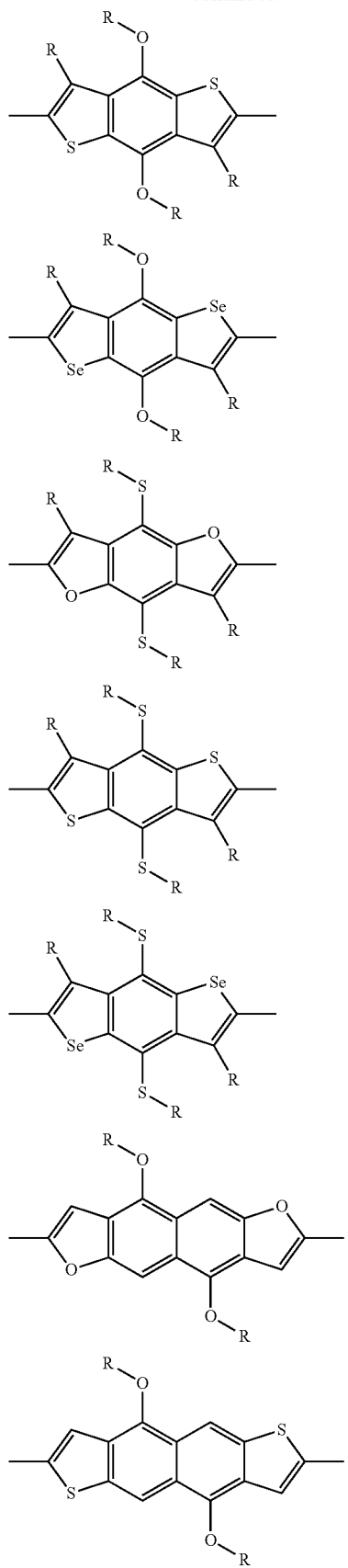

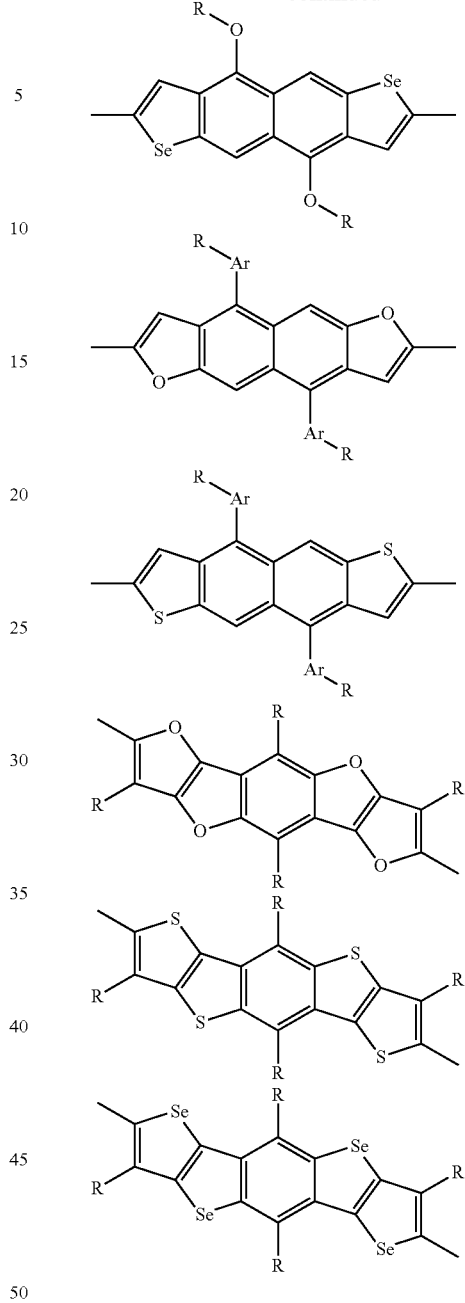

The number average molecular weight of the polymer may be in the range of about 1,000 to about 1,000,000 for some embodiments, with some embodiments having a number average molecular weight in the range of about 5,000 to about 500,000, and further embodiments having a number average molecular weight in the range of about 20,000 to about 200,000. It will be appreciated that molecular weight can be varied to select desired polymer properties. For example, lower molecular weight can promote solubility, while a higher molecular weight can promote film-forming properties.

Polymer Preparation

Polymers of formula (I) can be generally synthesized by co-polymerizing a monomer having the structure of formula (II) and a monomer having the structure of formula (III):

X—D—X (II)

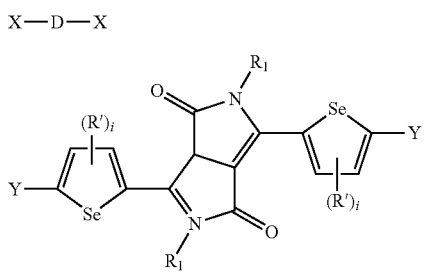
(III)

where $R_1$, R', i, and D are defined above. Each X and each Y can be, independently, a boronic acid group, a boronic acid ester group, a magnesium halide group, a zinc halide group, a trialkyl tin group, Cl, Br, or I.

Each X and each Y are chosen for complementary reactivity, i.e., such that under appropriate reaction conditions the carbon bound to X and the carbon bound to Y are linked by a new carbon-carbon bond. For example, in some embodiments, if X is selected from a boronic acid or a boronic acid ester group including, e.g., 1,3,2-dioxaborinane-2-yl, 4,4,5,5-tetramethyl-1,3,2-dioxaborolane-2-yl, and 5,5-dimethyl-1,3,2-dioxaborinane-2-yl; or a magnesium halide group including, e.g., magnesium chloride, magnesium bromide, and magnesium iodide; or zinc halide groups including, e.g., zinc chloride and zinc bromide; or trialkyltin groups including, e.g., trimethyl tin, triethyl tin, and tributyl tin; then Y can be selected from Cl, Br, or I. In other embodiments, if X is selected from Cl, Br, or I, then Y should be selected from a boronic acid or a boronic acid ester group including, e.g., 1,3,2-dioxaborinane-2-yl, 4,4,5,5-tetramethyl-1,3,2-dioxaborolane-2-yl, and 5,5-dimethyl-1,3,2-dioxaborinane-2-yl; or a magnesium halide group including, e.g., magnesium chloride, magnesium bromide, and magnesium iodide; or zinc halide groups including, e.g., zinc chloride and zinc bromide; or trialkyltin groups including, e.g., trimethyl tin, triethyl tin, and tributyl tin; then Y can be selected from Cl, Br, or I.

A method of making the polymers of formula (I) uses monomers as mentioned in formula (II) and (III) is shown as the following scheme.

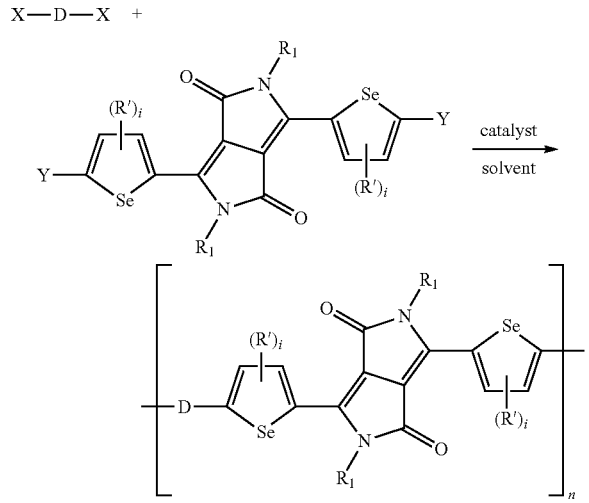

If the polymerization reaction is conducted between a dimagnesiohalo-arene compound and an arene dihalide compound, the polymerization reaction is a typical 'McCullough method', as reported by McCullough and Lowe (*J. Chem. Soc., Chem. Commun.* 1992, 70). In McCullough method, THF is used as a solvent commonly, and a mixture of toluene and THF can also be used sometimes. Some catalysts containing Pd or Ni, preferably [1,3-bis(diphenylphosphino)propane]dichloronickel(II) and tetrakis(triphenylphosphine)palladium(0), can be used as catalyst for this reaction, and the molar ratio between catalyst and starting material is in the range of 10-0.1%. The reaction can be conducted at about 10° C. to refluxing point of the solvent. Depending on the reactivities of the reactants, the polymerization may take 30 minutes to 24 hours. Dimagnesiohaloarene used in this reaction can be prepared from Grignard metathesis reaction, as reported by Loewe and McCullough (*Macromolecules*, 2001, (34), 4324-4333), or reaction between arene dihalide and magnesium.

In some embodiments, arene dihalide and Dimagnesiohalo-arene used in 'McCullough method' for the polymers of formula (I) are arene dibromide and dimagnesiobromoarene.

If the condensation polymerization reaction is conducted between a dizinchalo-arene compound and an arene dihalide compound, the polymerization reaction is a typical 'Rieke method', as reported by Chen and Rieke (*Synth. Met.* 1993, (60), 175). In this method, THF is used as a solvent commonly, and Some catalysts containing Pd or Ni, preferably [1,2-Bis(diphenylphosphino)ethane]dichloronickel(II), can be used as catalyst for this reaction, and the molar ratio between catalyst and starting material is in the range of 10-0.1%. The reaction is can be conducted at about 10° C. to refluxing point of the solvent. Depending on the reactivities of the reactants, the polymerization may take 30 minutes to 24 hours.

In some embodiments, arene dihalide and dizinchaloarene used in 'Rieke method' for the polymers of formula (I) are arene dibromide and dizincchloro-arene.

If the condensation polymerization reaction is conducted between a bis(trialkylstannyl)-arene compound and an arene dihalide, the polymerization reaction is a typical 'Stille coupling method', as reported by Iraqi and Barker (*J. Mater. Chem.* 1998, (8) 25). In this method, many kinds of solvents including, but not limited to, tetrahydrofuran (THF), Dimethyl Formamide (DMF), and toluene can be used as a solvent commonly, and Some catalysts containing Pd, preferably tetrakis(triphenylphosphine)palladium(0), can be used as catalyst for this reaction, and the molar ratio between catalyst and starting material is in the range of 10-0.1%. The reaction can be conducted at about 60° C. to refluxing point of the solvent. Depending on the reactivities of the reactants, the polymerization may take 1 to 72 hours.

In some embodiments, arene dihalide and dizinchaloarene used in 'Stille coupling method' for the polymers of formula (I) are arene dibromide and dizincchloro-arene.

If the condensation polymerization reaction is conducted between an arene-diboronic acid compound or an arene-diboric acid ester compound and an arene dihalide, the polymerization reaction is a typical 'Suzuki reaction', as reported by Miyaura and Suzuki (*Chemical Reviews* 1995 (95): 2457-2483). In this method, many kinds of solvents including, but not limited to, THF, and toluene can be used as a solvent commonly, and Some catalysts containing Pd, preferably tetrakis(triphenylphosphine)palladium(0), can be used as catalyst for this reaction, and the molar ratio between catalyst and starting material is in the range of 10-0.1%. The reaction can be conducted at about 60° C. to refluxing point of the solvent.

In some embodiments, a suitable arene dihalide used in 'Suzuki reaction' for the polymers of formula (I) can be arene dibromide or dizincchloro-arene.

Devices

Generally, the polymers of formula (I) are useful in any application wherein a conjugated polymer, particularly a conjugated photovoltaic polymer, would have utility. For example, the present polymers are suitable as the active materials in the following devices: thin film semiconductor devices such as solar cells, NIR light emitting diodes, transistors, NIR photo-detectors, and photoconductors; electrochemical devices such as rechargeable batteries, capacitors, supercapacitors, and electrochromic devices, and sensors.

Semiconductive compositions may be prepared that comprise a polymer of formula (I) optionally combined with an admixer, such as a compound selected such that charge and/or energy transfer takes place between the admixer and the polymer when an excitation source including light or voltage is applied across the composition. For example, the admixer can be fullerene such as: $C_{60}$, $C_{70}$, or $C_{80}$, or some substituted fullerene compounds such as $PC_{60}BM$ ([6,6]-phenyl $C_{61}$ butyric acid methyl ester) and $PC_{71}BM$ ([6,6]-phenyl $C_{71}$ butyric acid methyl ester).

In some embodiments, polymers of formula (I) may be used as photovoltaic materials in photovoltaic devices such as photodetector devices, solar cell devices, and the like. Photovoltaic devices, including solar cell devices, are generally comprised of laminates of a suitable photovoltaic material between a hole-collecting electrode layer and an electron-collecting layer. Additional layers, elements or a substrate may or may not be present.

FIG. 1 is a schematic illustration of an electro-optic device 100 according to an embodiment. The electro-optic device 100 has a first electrode 102, a second electrode 104 spaced apart from the first electrode 102, and an active layer 106 disposed between the first electrode and the second electrode. The electro-optic device 100 can have multiple layers of active materials and/or layers of material between the electrodes and the active layer such as the layer 108, for example. The active layer can include a conjugated polymer material according to one or more embodiments. One or both of the electrodes 102 and 104 can be transparent electrodes in some embodiments.

Figure 3A:
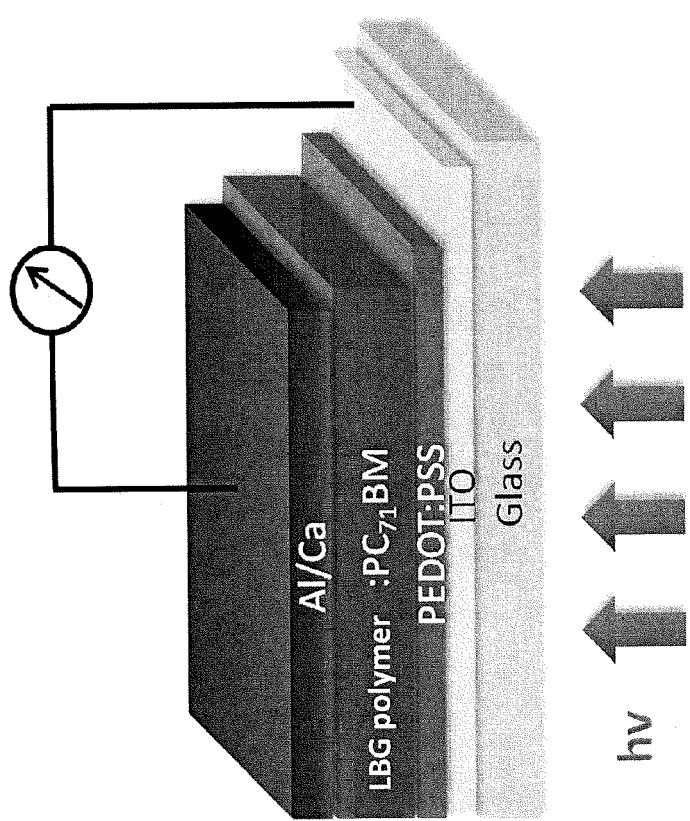

FIG. 3 is a schematic illustration of PSC device according to a specific embodiment. The device in FIG. 3A has a first electrode Ca/Al, a second electrode PEDOT/ITO spaced apart from the first electrode, and an active layer Polymer: $PC_{71}BM$ disposed between the first electrode and the second electrode. The device in FIG. 3B has a first electrode TiO2-silver nanowire composite (transparent), a second electrode PEDOT/ITO spaced apart from the first electrode, and an active layer Polymer:$PC_{71}BM$ disposed between the first electrode and the second electrode. The active layer can include a conjugated polymer material according to one or more embodiments. One or both of the electrodes can be other metals, electrolytes and transparent electrodes in some embodiments.

The schematic illustrations of FIGS. 1 and 3 are shown as examples. Devices according to other embodiments are not limited to these specific examples.

Tandem Devices

In some embodiments, the device is a tandem device having more than one active layer. In some embodiments, the tandem device may be an inverted tandem device.

FIG. 2 is a schematic illustration of a tandem electro-optic device 200 according to an embodiment. The electro-optic device 200 has a first electrode 202, a second electrode 204 spaced apart from the first electrode 202, and an active layer 206 disposed between the first electrode and the second electrode. This embodiment is an example of a tandem electro-optic device that has a second active layer 210 between the first electrode 202 and the second electrode 204. The electro-optic device 200 can have additional layers of material between the active layers and the electrodes and/or between the two active layers. For example, there could be a layer 208 between the active layers 206 and 210. The devices are not limited to only one or two active layers; they may have multiple active layers in some embodiments. One or both of the electrodes can be other metals, electrolytes and transparent electrodes in some embodiments.

Figure 4B:
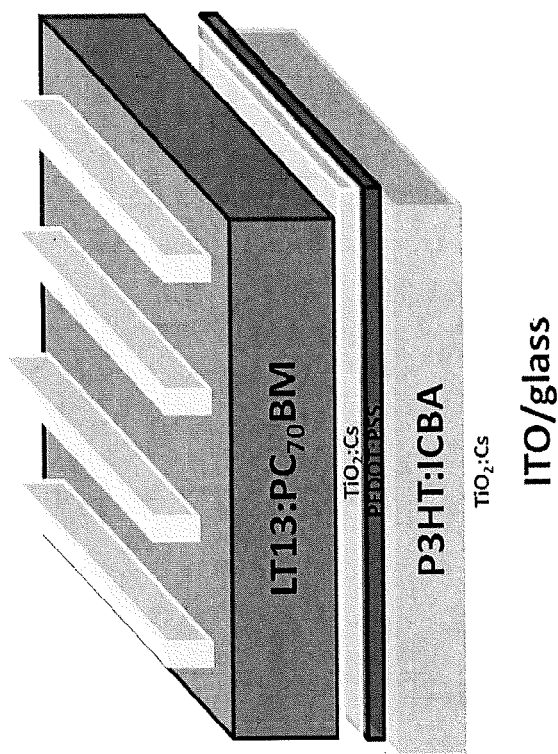
FIGS. 4A-4B are schematic illustrations of tandem polymer solar cell devices.
Figure 4A:
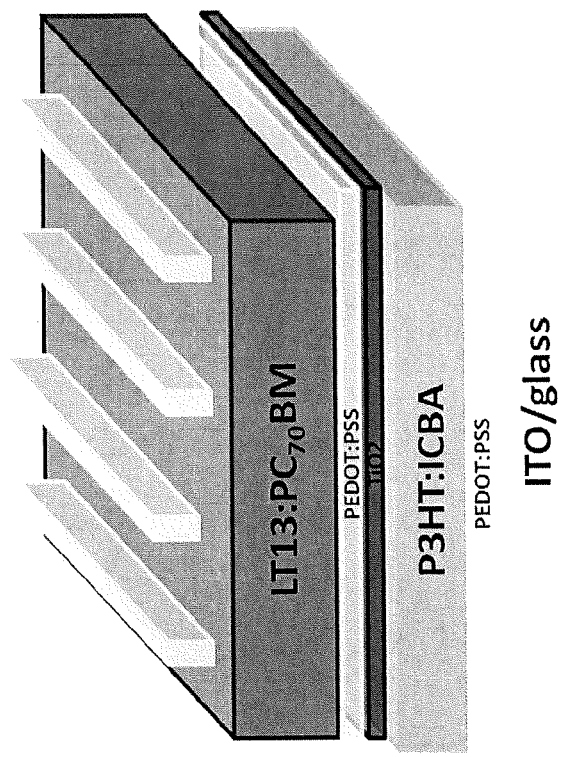

FIGS. 4A-4B are schematic illustrations of tandem PSC device according to another embodiment. Based on FIG. 3, a device with multiple active layers with/without thin interfacial layers between different layers of active materials is illustrated. For example, a tandem photovoltaic cell that has two or more active layers with thin interfacial layers.

The schematic illustrations of FIGS. 2 and 4A-4B are shown as examples. Devices according to other embodiments are not limited to these specific examples.

Although the photoactive materials play a critical role in determining the PCE, there have been no reports so far on designing photoactive materials for high efficiency tandem PSCs. To be applied in a tandem structure effectively, there are several requirements for rear cell LBG polymers. First, a small energy bandgap (<1.5 eV) is critical so that the overlap of absorptions between the front cell and rear cell can be minimized (Dennler et al., Adv. Mater., vol. 20, p. 579, 2008). Second, fine-tuning of the HOMO and the LUMO levels is required to achieve $V_{OC}$ with a small bandgap while maintaining a proper LUMO level for efficient charge separation (Huo et al., Angew. Chem. Int. Ed., vol. 49, p. 1500, 2010; Scharber et al., Adv. Mater., vol. 18, p. 789, 2006. Third, high charge carrier mobility and fine phase separation with the acceptor are required for high $J_{SC}$ and FF in single cell devices (Bijleveld et al., J. Am. Chem. Soc., vol. 131, p. 16616, 2009). Since the two cells are connected in series, the total current will be limited by the sub-cell with the lower current. Obtaining high current in the rear cell is a challenge because part of the incident light will have already been absorbed by the front cell, so the current it can provide will be lower than in a single cell device. Therefore, a carefully designed LBG polymer will be suitable for tandem cells only if it can achieve high current by efficiently utilizing the low energy (<2 eV) portion of the solar spectrum.

Transparent Solar Cell Devices

FIG. 1 is also a schematic illustration of a transparent solar cell device according to an embodiment. This embodiment is an example of a solar cell device that both of first electrode 102 and second electrode 104 are visibly transparent. For example, a nano-scaled electronic structure which human being's eyes cannot determine will be applied.

The devices are not limited to only one or two active layers; they may have multiple active layers in some embodiments.

FIG. 3B is a schematic illustration of transparent solar cell device according to another embodiment. The device in FIG.

6 has a first electrode composed of TiO$_2$ nanoparticles/Silver nanowires (AgNW), a second electrode PEDOT:PSS/ITO spaced apart from the first electrode, and an active layer Polymer:PC$_{61}$BM disposed between the first electrode and the second electrode. The active layer can include a conjugated polymer material according to one or more embodiments. One or both of the electrodes can be other nanostructures, nanoparticles, electrolytes and transparent electrodes in some embodiments.

The schematic illustrations of FIGS. 3A-3B are shown as examples. Devices according to other embodiments are not limited to these specific examples.

To be a good transparent solar cell, polymer materials as the active layer desirably have certain properties. A small energy bandgap (for example, <1.5 eV) avoids the absorption of sunlight of visible region (typically in the wavelength region of 400-700 nm). In addition, the polymers desirably have properties as described above to enhance device performance, such as high mobility, strong intermolecular interaction, and suitable molecule energy level. It thus would be desirable according to some embodiments to provide conjugated polymers as photovoltaic materials that possess some or all of the properties mentioned above.

NIR Light Emitting Diode

FIG. 1 is also a schematic illustration of an organic NIR LED device according to an embodiment. The electro-optic device 100 has a first electrode 102, a second electrode 104 spaced apart from the first electrode 102, and an active layer 106 disposed between the first electrode and the second electrode. The electro-optic device 100 can have multiple layers of active materials and/or layers of material between the electrodes and the active layer such as the layer 108, for example. The active layer can include a conjugated polymer material according to one or more embodiments. One or both of the electrodes 102 and 104 can be transparent electrodes in some embodiments.

The devices are not limited to only one or two active layers; they may have multiple active layers in some embodiments.

Figure 5:
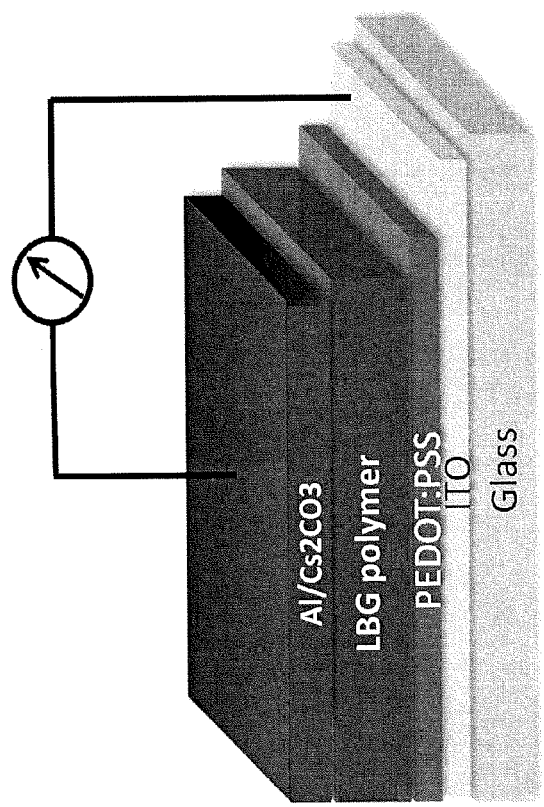
FIG. 5 is a schematic illustration of a transparent solar cell device.

FIG. 5 is a schematic illustration of transparent solar cell device according to another embodiment. The device in FIG. 5 has a first electrode composed of Al/Cs$_2$CO$_3$, a second electrode PEDOT:PSS/ITO spaced apart from the first electrode, and an active layer of the LBG polymer disposed between the first electrode and the second electrode. The active layer can include a conjugated polymer material according to one or more embodiments. One or both of the electrodes can be other nanostructures, nanoparticles, electrolytes and transparent electrodes in some embodiments.

The schematic illustrations of FIG. 5 are shown as examples. Devices according to other embodiments are not limited to these specific examples.

NIR Photo-Detectors

FIG. 1 is also a schematic illustration of an organic NIR photo-detector device according to an embodiment. The electro-optic device 100 has a first electrode 102, a second electrode 104 spaced apart from the first electrode 102, and an active layer 106 disposed between the first electrode and the second electrode. The electro-optic device 100 can have multiple layers of active materials and/or layers of material between the electrodes and the active layer such as the layer 108, for example. The active layer can include a conjugated polymer material according to one or more embodiments. One or both of the electrodes 102 and 104 can be transparent electrodes in some embodiments.

The devices are not limited to only one or two active layers; they may have multiple active layers in some embodiments.

Figure 6:
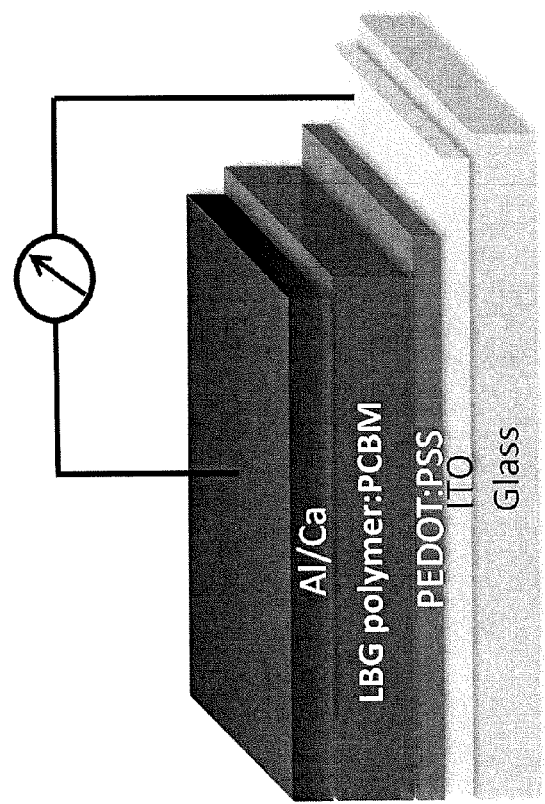
FIG. 6 is a schematic illustration of a NIR photo-detector device.

FIG. 6 is a schematic illustration of a NIR photo-detector device according to another embodiment. The device in FIG. 6 has a first electrode composed of Al/Ca, a second electrode PEDOT:PSS/ITO spaced apart from the first electrode, and an active layer of the polymer:PCBM blend disposed between the first electrode and the second electrode. The active layer can include a conjugated polymer material according to one or more embodiments. One or both of the electrodes can be other nanostructures, nanoparticles, electrolytes and transparent electrodes in some embodiments.

The schematic illustrations of FIG. 6 are shown as examples. Devices according to other embodiments are not limited to these specific examples.

EXAMPLES

Temperature used in the following examples is in degrees C., and the pressure is at or near atmospheric. All solvents were purchased as HPLC grade, and all reactions were routinely conducted under an inert atmosphere of argon. All reagents were obtained commercially unless otherwise indicated.

Example 1

Synthesis of LJ01

Synthesis of poly{2,6'-4,8-di(5-ethylhexylthienyl)benzo[1,2-b; 3,4-b]dithiophene-alt-2,5-bis(2-butyloctyl)-3,6-bis(selenophene-2-yl)pyrrolo[3,4-c]pyrrole-1,4-dione}, LJ01

Synthetic route of this polymer, LJ01 is shown in the following scheme.

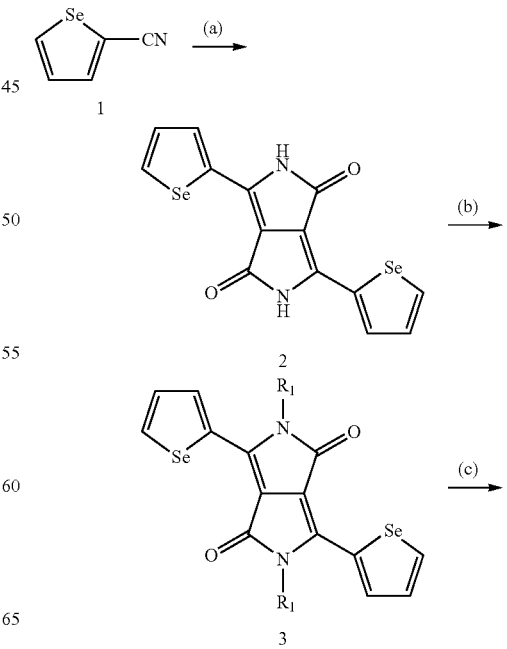

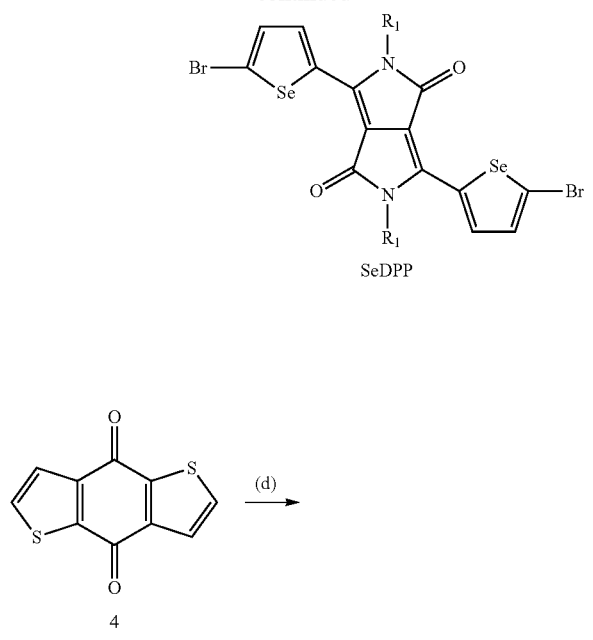
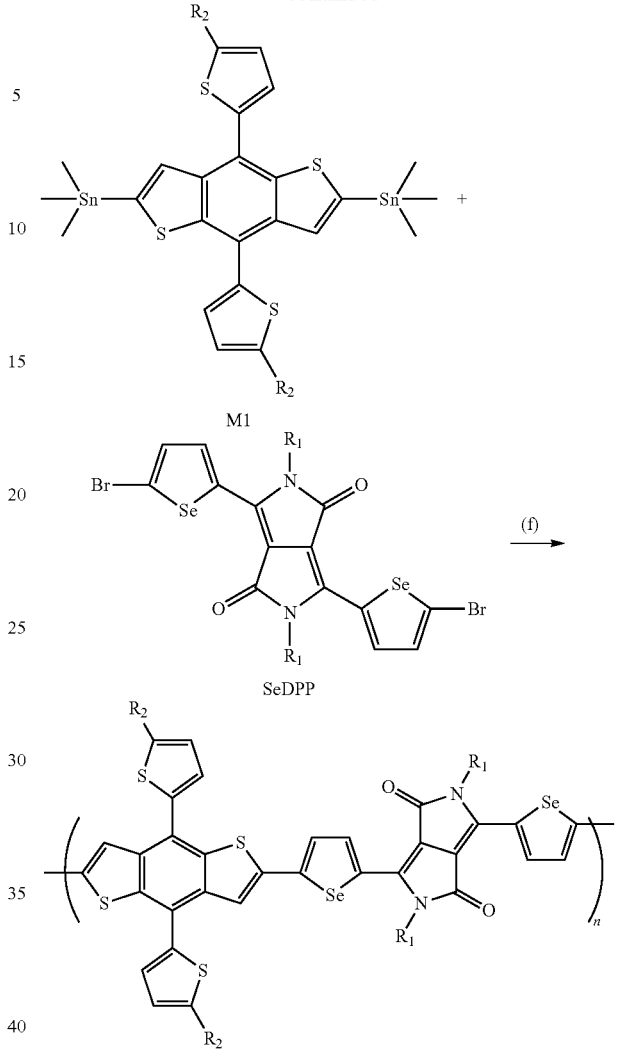
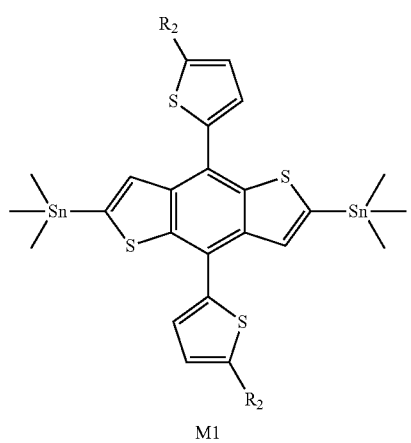

Where Selenophene-2-carbonitrile (1) was synthesized according to literature (Shahid et al., *Chem. Sci.*, vol. 3, p. 181, 2012.)

3,6-Dithiophen-2-yl-2,5-dihydropyrrolo[3,4-c]pyrrole-1,4-dione (2)

Sodium (1.54 g, 67.2 mmol) was added to a two-neck round bottom flask with nitrogen protection. 2-methyl-2-butanol (38 mL) was subsequently added, and followed by heating up the solution to 110° C. until the sodium was totally consumed. After cooled down the solution to 65° C., the compound 1 (7.0 g, 44.9 mmol) was injected in one portion. The mixture was stirred for another 20 min, and then diisopropyl succinate (3.94 g, 19.5 mmol) was slowly dropped in 1 h. The reaction temperature was gradually increased to 70° C. and kept for about 1 h. Then the solution was further heated to 80° C. and stirred for an additional 11 h. Finally, the mixture was cooled to 0° C., diluted with 20 mL methanol, and neutralized by stirring with acetic acid. After 2 h, the suspension was filtered, and the black filter cake was washed with methanol and water twice and dried in vacuum to obtain a dark purple crude product that could be used directly without further purification (6.2 g, yield 81%).

2,5-Di(2-octyldodecyl)-3,6-bis-(selenophenyl)-1,4-diketopyrrolo[3,4c]pyrrole (3)

Compound 2 (2.9 g, 7.4 mmol), 18-crown-6 (~20 mg), and anhydrous potassium carbonate (4.57 g, 33.1 mmol) were dissolved into N,N-dimethylformamide (50 ml) in a two-neck round flask under nitrogen protection. 2-butyloctyl bromide (7.3 g, 29.4 mmol) was injected in one portion by syringe, and gradually heated to 120° C. After 4 h, the reaction was further heated to 135° C. with stirring for another 8 h. The reaction mixture was the cooled to room temperature, poured into 100 mL of ice water and extracted with dichloromethane. The combined extracts were washed with water several times, and the solvent was then removed under reduced pressure. After drying, the crude product was purified by silica gel chromatography using a dichloromethane and hexane mixture as the eluent to obtain a purple-red solid (1.1 g, 20%).

2,5-Di(2-octyldodecyl)-3,6-bis-(5-bromoselenophenyl)-1,4-diketopyrrolo[3,4c]pyrrole (SeDPP)

Compound 3 (0.74 g, 1.0 mmol) and N-bromosuccinimide (0.38 g, 2.1 mmol) were dissolved into chloroform (20 mL) in a two-neck round bottom flask under nitrogen protection, then the reaction mixture was protected from light and stirred at room temperature overnight. The mixture was then poured into methanol (100 mL) and then filtered. The filtered cake was washed with hot water and methanol twice. After drying in a vacuum, the pure product was obtained as dark-purple solid (0.7 g, 78%).

4,8-bis(5-decyl-2-thienyl)-benzo[1,2-b:4,5-b']dithiophene (4)

Under the protection of argon, n-butyllithium (2.88 M, 11.4 mL) was added dropwise to 2-decylthiophene (6.73 g, 30.0 mmol) in THF (30 mL) at 0° C.; then the mixture was warmed up to 50° C. and stirred for 1 h. Subsequently, 4,8-dehydrobenzo[1,2-b:4,5-b']dithiophene-4,8-dione (1) (1.76 g, 8.0 mmol) was added, and the mixture was stirred for 1 h at 50° C. After cooling down to ambient temperature, SnCl$_2$.2H$_2$O (13.5 g, 60 mmol) in 10% HCl (20 mL) was added, and the mixture was stirred for an additional 1.5 h and poured into ice water. The mixture was extracted by diethyl ether twice, and the combined organic phase was concentrated. Further purification was carried out by column chromatography using petroleum ether as eluent to obtain pure 2 as a light yellow solid (3.0 g, yield 59.0%).

2,6-Bis(trimethyltin)-4,8-bis(5-decyl-2-thienyl)-benzo[1,2-b:4,5-b']dithiophene (M1)

Under the protection of argon, n-butyllithium (2.88 M, 1.30 mL) was added dropwise to compound 2 (0.942 g, 1.48 mmol) in THF (20 mL) at room temperature and stirred for 2 h at 50° C. Then trimethyltin chloride in hexane (1.0 M, 4.5 mL) was added in one portion at room temperature. After 6 h, the reaction was stopped and water (20 mL) was added, and then the mixture was extracted by diethyl ether twice. After removing the solvent, the residue was purified by recrystallization from hot ethanol to obtain pure M1 as a yellow solid (1.05 g, yield 73.9%).

LJ01

M1 (0.2360 g, 0.2456 mmol) and compound SeDPP (0.1952 g, 0.2456 mmol) were dissolved into 10 mL toluene and 1 mL DMF in a flask protected by argon. The solution was flushed with argon for 10 minutes, then 10 mg of Pd(PPh$_3$)$_4$ was added into the flask. The solution was flushed with argon again for another 10 minutes. The oil bath was heated to 115° C. gradually, and the reaction mixture was stirred for 8 hours at 115° C. under argon atmosphere. Then, the mixture was cooled down to room temperature and the polymer was precipitated in 100 ml methanol and the precipitated solid was collected and purified by silica gel chromatography using chloroform as eluent. The polymer was obtained as dark green-purple solid, yield 56%. The polymer can be readily dissolved into chloroform, chlorobenzene or dichlorobenzene, etc.

Figure 7B:
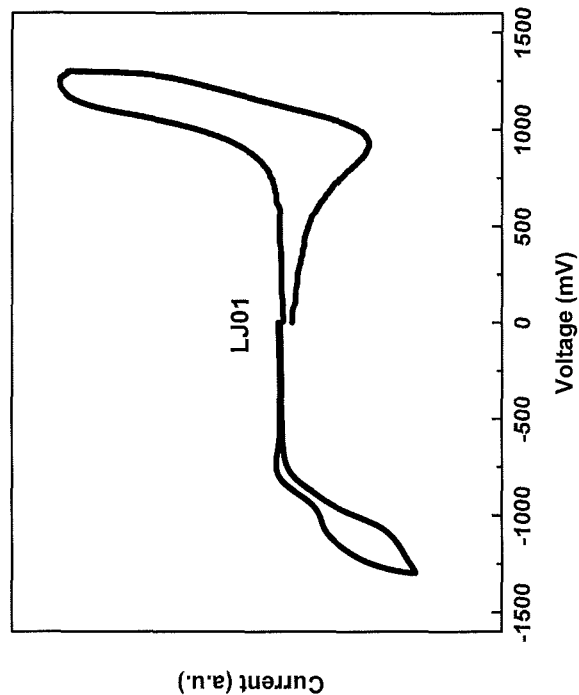
FIGS. 7A-7B shows the UV/Vis absorption spectrum (FIG. 7A) in $CHCl_3$ and film and electrochemical cyclic voltammetry spectrum (FIG. 7B) of LJ01.
Figure 7A:
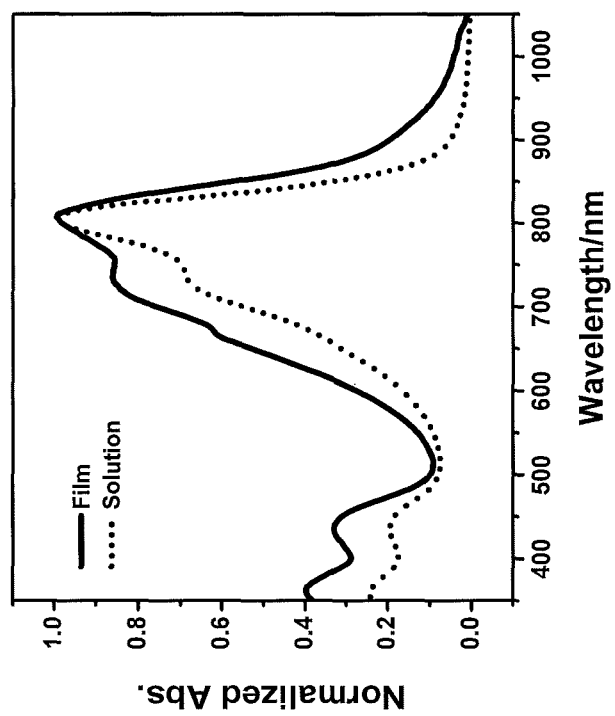

FIG. 7 shows the UV/Vis absorption spectrum (FIG. 7A) in CHCl$_3$ and film and electrochemical cyclic voltammetry spectrum (FIG. 7B) of LJ01. The molecular weight (Mn) of LJ01 was found to be 38.0 k.

Example 2

Synthesis of LJ08

Synthetic route of LJ08 is shown in the following scheme.

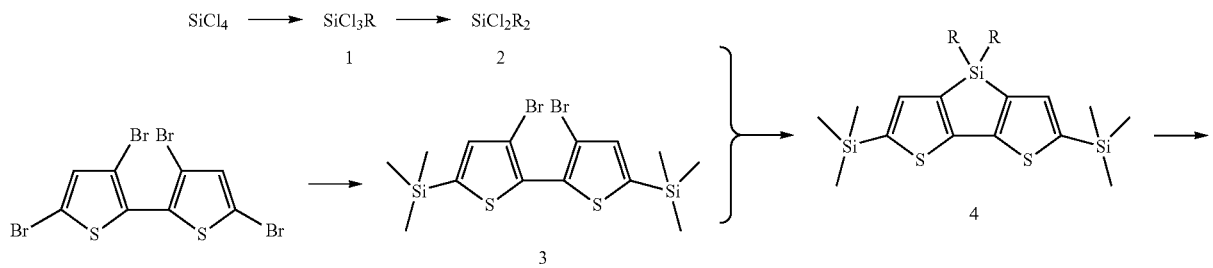

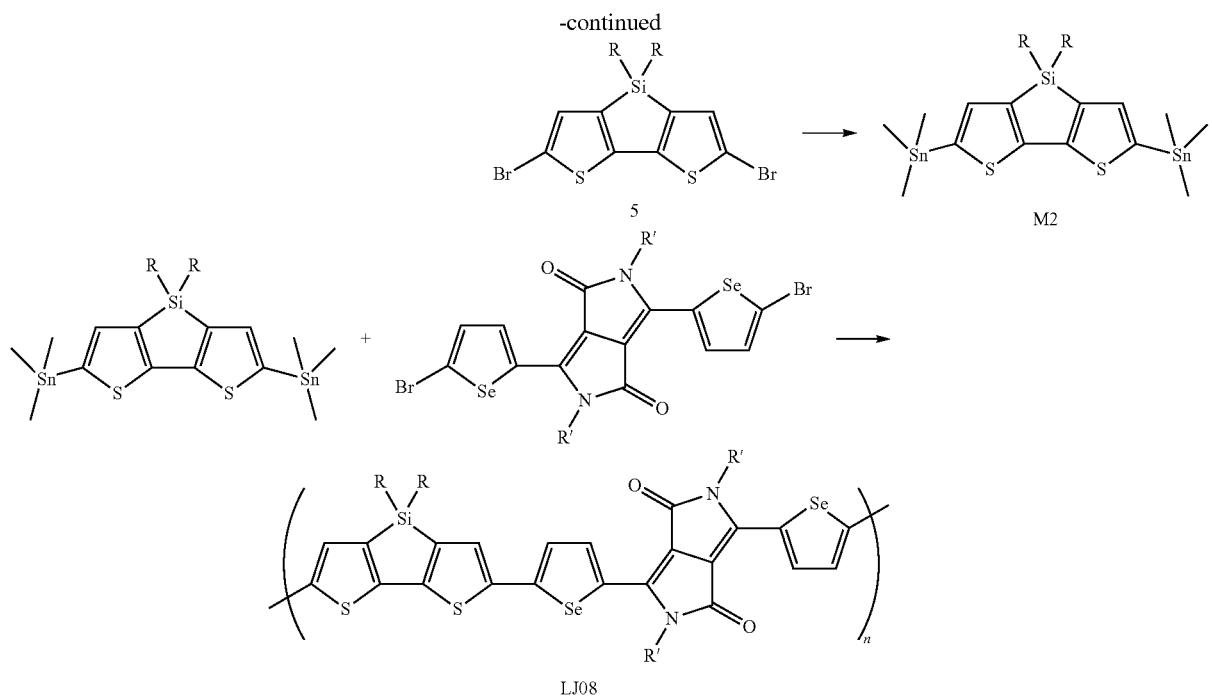

R = 2-ethylhexyl, R' = 2-butyloctyl

Trichloro(2-ethylhexyl)silane, 1

In a 250 ml flask, silicon tetrachloride 23 ml (34 g, 0.2 mol) and 60 ml of THF were put together and cooled down to 0° C. by ice-salt bath. 100 ml of 2-Ethylhexyl-magnesium bromide purchased from Aldrich Company (1 mol/L, in ether) was added dropwise. Addition was accompanied by the formation of magnesium salts which precipitated. When all of Grignard reagent was added, the ice-bath was removed. After 12 hours of stirring under ambient temperature, the reaction product was poured into 600 ml of hexane and then filtered by suction. The magnesium salts was washed with hexane for several times. Upon removal of the volatile solvent, the residue oil was distilled under vacuum. Compound 1 was obtained as colorless oil (18.8 g, yield 76%).

Dichloro-bis(2-ethylhexyl)silane, 2

Compound 1 (15 g, 60 mmol) and 80 ml THF was put into a 250 ml flask and cooled down to 0° C. by ice-salt bath, in which 50 ml of 2-Ethylhexyl-magnesium bromide (1 mol/L, in ether) was added dropwise. After 12 hours of stirring under ambient temperature, the volatile solvent was removed by rotatory evaporator. The sticky residue was washed by 300 ml hexane and filtered by suction. The filtrate was collected, and after removal of the volatile solvent, the residue oil was distilled under vacuum. Compound 2 was obtained as colorless oil (11.4 g, yield 71%).

3,3'-Dibromo-5,5'-bis(trimethylsilyl)-2,2'-bithiophene, 3

4.78 g (10 mmol) of 3,3',5,5'-tetrabromo-2,2'-bithiohpene was dissolved into 150 ml ultra dry THF, and the solution was cooled down to −90° C. by a methanol-liquid nitrogen bath. Then, 8 ml butyllithium solution in hexane (2.5 mol/L) was added dropwise over a period of 1 hour. After addition of butyllithium, the reactant was stirred for 15 minutes. Subsequently, 2.7 g chlorotrimethylsilane (25 mmol) was added in one portion, and temperature of the reactant was rise to ambient temperature by removal cooling bath. Then, the reactant was poured into water and extracted by ethyl ether for several times. The volatiles were removed under vacuum. The residue was purified by silica gel chromatography using hexane as eluent and then by recrystallization using ethanol as solvent and gave out 3.3 g of 3,3'-dibromo-5,5'-bis(trimethylsilyl)-2,2'-bithiophene (yield 71%), compound 3, as a white solid.

4,4'-Bis(2-ethyl-hexyl)-5,5'-bis(trimethylsilyl)-dithieno[3,2-b:2',3'-d]silole, 4

Compound 3 (2.34 g, 5 mmol) and 40 ml THF were put into a flask, and cooled down to −78° C. by a liquid nitrogen-acetone bath. Then, 3.9 ml butyllithium solution in hexane (2.7 mol/L) was added dropwise in 5 minutes, and the reactant was stirred for another 15 minutes at that temperature. Subsequently, 1.95 g dichlorodi(2-ethyl-hexyl)silane (6 mmol) was added in one portion, and the cooling bath was removed and the reactant was stirred for 2 hours under ambient temperature. Then, the reactant was poured into water and extracted by ethyl ether for several times. The volatiles were removed under vacuum. The residue was purified by silica gel chromatography using hexane as eluent and gave 2.26 g of 3,3'-bis(2-ethyl-hexyl)-silyene-5,5'-bis(trimethylsilyl)-2,2'-bithiophene (yield 72%), compound 4, as colorless oil.

4,4'-Bis(2-ethyl-hexyl)-5,5'-dibromo-dithieno[3,2-b:2',3'-d]silole, 5

Compound 4 (1.69 g, 3 mmol) was dissolved into 20 ml THF, and N-bromosuccinimide (1.1 g, 6.17 mmol) was added in one portion. The reactant was stirred at ambient temperature for 4 hours, and then extracted by diethyl ether. The volatiles were removed under vacuum, and the residue was purified by silica gel chromatography using hexane as eluent. 4,4'-Bis(2-ethyl-hexyl)-5,5'-dibromo-dithieno[3,2-b: 2',3'-d]silole (1.37 g, 2.9 mmol), compound 5, was obtained as sticky colorless or pale yellow oil with a yield of 96%.

4,4'-Bis(2-ethyl-hexyl)-5,5'-bis(trimethyltin)-dithieno[3,2-b:2',3'-d]silole, M2

Compound 5 (1.2 g, 2.51 mmol) and 20 ml ultra dry THF were put into a flask. The clear solution was cooled down to −78° C. by a liquid nitrogen-acetone bath. Then, 2.4 ml butyllithium solution in hexane (6.5 mmol, 2.7 mol/L) was added dropwise. After stirring at −78° C. for 15 minutes, 7 ml trimethyltin chloride was added in one portion, and then the cooling bath was removed. After being stirred at ambient temperature for two hours, the reactant was poured into cool water and extracted by diethyl ether for several times. After removal of volatiles, 4,4'-Bis(2-ethyl-hexyl)-5,5'-bis(trimethyltin)-dithieno[3,2-b:2',3'-d]silole (1.78 g, 2.39 mmol), compound 6, was obtained as sticky pale green oil with a yield of 95.6% and used without any further purification.

LJ08

M2 (0.2360 g, 0.2456 mmol) and compound SeDPP (0.1952 g, 0.2456 mmol) were dissolved into 10 mL toluene and 1 mL DMF in a flask protected by argon. The solution was flushed with argon for 10 minutes, then 10 mg of Pd(PPh$_3$)$_4$ was added into the flask. The solution was flushed with argon again for another 10 minutes. The oil bath was heated to 115° C. gradually, and the reaction mixture was stirred for 8 hours at 115° C. under argon atmosphere. Then, the mixture was cooled down to room temperature and the polymer was precipitated in 100 ml methanol and the precipitated solid was collected and purified by silica gel chromatography using chloroform as eluent. The polymer was obtained as dark green-purple solid, yield 63%. The polymer was readily dissolved into chloroform, chlorobenzene or dichlorobenzene, etc.

The polymer showed absorption onset at 1050 nm. The molecular weight (Mn) of LJ08 was found to be 29.0 k.

Example 3

Fabrication and Characterization of PSC Device

The polymer, LJ01, (30 mg) was dissolved in chlorobenzene to make 7.5 mg ml$^{-1}$ solution, followed by blending with PC$_{71}$BM (60 mg).

PSC devices were fabricated on a transparent, indium-tin oxide (ITO) coated glass substrate. A thin layer of a conducting polymer, poly(styrenesulfonate) doped poly(3,4-ethylenedioxy-thiophene) (PEDOT:PSS), was spin-coated onto the ITO surface for a better interface. The thickness of the PEDOT:PSS layer was about 30 nm, measured with Dektek profilometer. Then, a thin layer was spin-coated using the solution prepared above. Then, thin layers of calcium and aluminum were evaporated successively at pressure around 10$^{-4}$ Pa. Testing was performed in a N$_2$ filled glove box under AM 1.5G irradiation (100 mW cm$^{-2}$) using a Xenon lamp solar simulator calibrated with a silicon diode calibrated in National Renewable Energy Laboratory (NREL).

Figure 8:
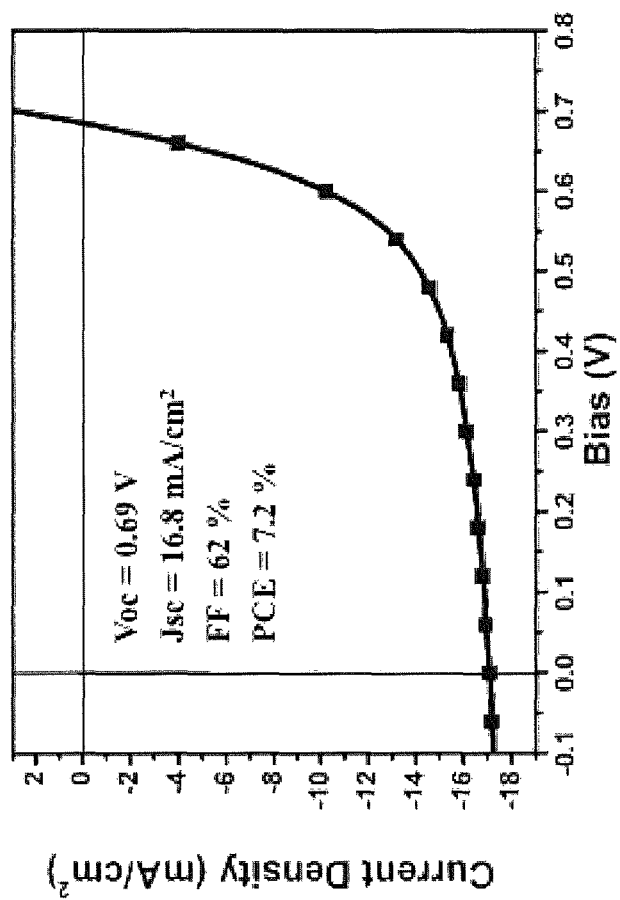
FIG. 8 shows I-V curve data of a polymer solar cell device.

FIG. 8 shows I-V curve data of a PSC device under simulated sunlight (AM 1.5, 100 mW/cm$^2$) with a structure of ITO.PEDOT:PSS/LJ01:PC$_{71}$BM/Ca/Al according to an embodiment. The PCE of the best PSC device was 7.2%, with a V$_{OC}$ of 0.69 V, a J$_{SC}$ of 16.8 mA/cm$^{-2}$, and a FF of 62%.

Example 4

Fabrication and Characterization of Polymer Tandem Solar Cell Device

Photovoltaic cells were fabricated on indium tin oxide (ITO) coated glass substrates. A TiO$_2$:Cs solution prepared by blending 0.5 and 0.2 wt % solutions of TiO$_2$ and Cs$_2$CO$_3$ in a 1:1 volume ratio was spin-casted at 3000 rpm for 30 s, and the thermal annealing was performed at 80° C. for 20 min. The poly(3-hexylthiophene) (P3HT):Indene-C$_{60}$ bisadduct (ICBA) (P3HT:ICBA) at a 1:0.7 weight ratio in 1% chloroform solution was spin-casted at 4000 rpm for 30 s. A modified PEDOT:PSS layer was spin-casted at 4000 rpm for 60 s on top of the P3HT:ICBA layer. Another thin layer of TiO$_2$:Cs was spin-coated and then a layer of LJ01:PC$_{71}$BM was spin-coated. Finally, the device fabrication was completed by thermal evaporation of 80 nm Al as the cathode.

Figure 9B:
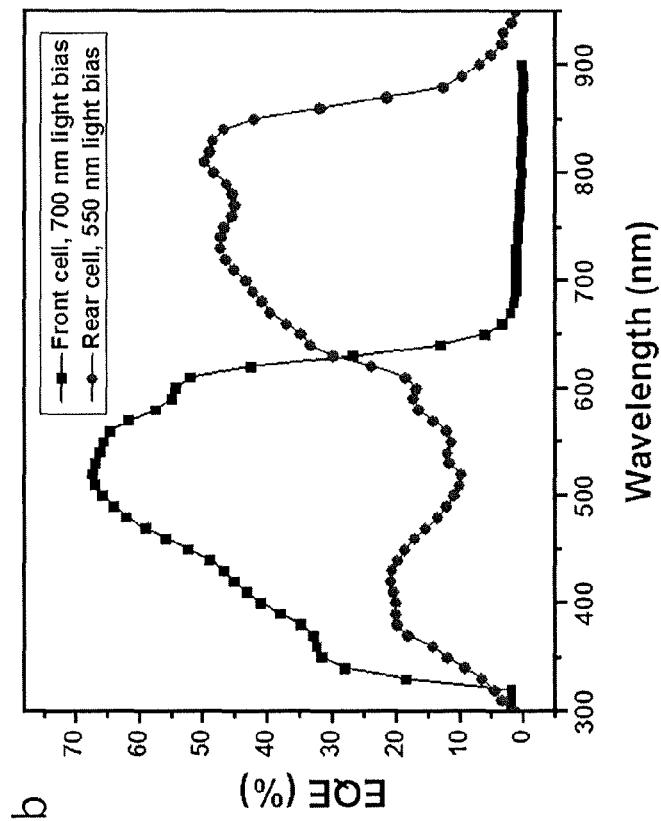
FIG. 9A and FIG. 9B show I-V curve and EQE data of an inverted polymer tandem solar cell device.
Figure 9A:
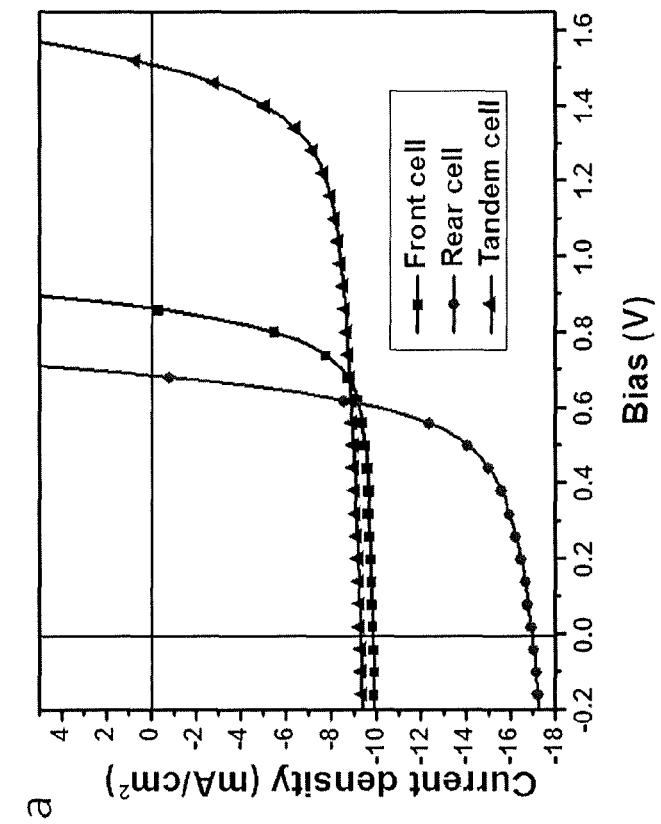

FIG. 9A and FIG. 9B shows I-V curve and EQE data of a inverted polymer tandem solar cell device under simulated sunlight (AM 1.5, 100 mW/cm$^{-2}$) according to an embodiment. The PCE of the best tandem PSC device was 9.4%, with an V$_{OC}$ of 1.52 V, a J$_{SC}$ of 9.4 mA/cm$^{-2}$, and a FF of 66%.

Example 5

Fabrication and Characterization of Visibly-Transparent Solar Cell Devices

Visibly transparent PSCs were fabricated on patterned ITO-coated glass substrates. The PEDOT:PSS layer was spin-cast at 4000 rpm for 60 s and annealed at 120° C. for 15 min in air. The LJ01:PCBM blend with a weight ratio of 1:2 in dichlorobenzene solution (0.8 wt %) was spin-cast at 2500 rpm for 80 s on top of the PEDOT:PSS layer to form a ~100 nm thick active layer. A TiO$_2$ sol-gel solution was then spin-coated onto the active layer at 2500 rpm for 30 s and annealed at 100° C. for 1 min to form the n-type interface layer. For the deposition of the AgNW-based composite electrode, the silver nanowire dispersion in isopropyl alcohol was spin-coated (2 mg/mL dispersion, 2500 rpm, 10 drops) onto the TiO$_2$ layer to form AgNW conducting networks. The fusing process of the silver nano-wire network was then carried out by applying diluted TiO$_2$ sol-gel solution in ethanol at 3000 rpm and baking at 100° C. for 10 s. The ITO nanoparticle dispersion (10 wt %) was used as transparent conductive filler and was spin-coated onto the fused AgNW matrix to form the composite electrode. Mild heating at 80° C. for 1 min removed the residual solvent. The thickness of the transparent composite electrode is around 400 nm. The device electrode fingers were formed by cutting the films with a blade and blowing the devices with N$_2$ to avoid possible short circuits between the top AgNWs and the bottom ITO substrate. The active area is 0.10 cm$^2$, which is defined by the overlap between bottom ITO substrate and the top fingers.

Figure 10B:
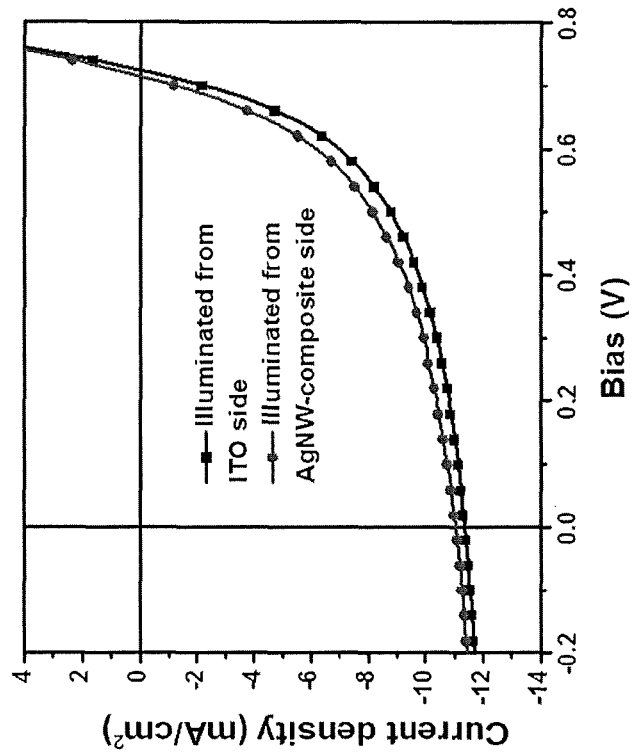
FIG. 10A shows the transmission spectrum and a photograph and FIG. 10B shows the current density-voltage characterization of a visibly-transparent polymer solar cell.
Figure 10A:
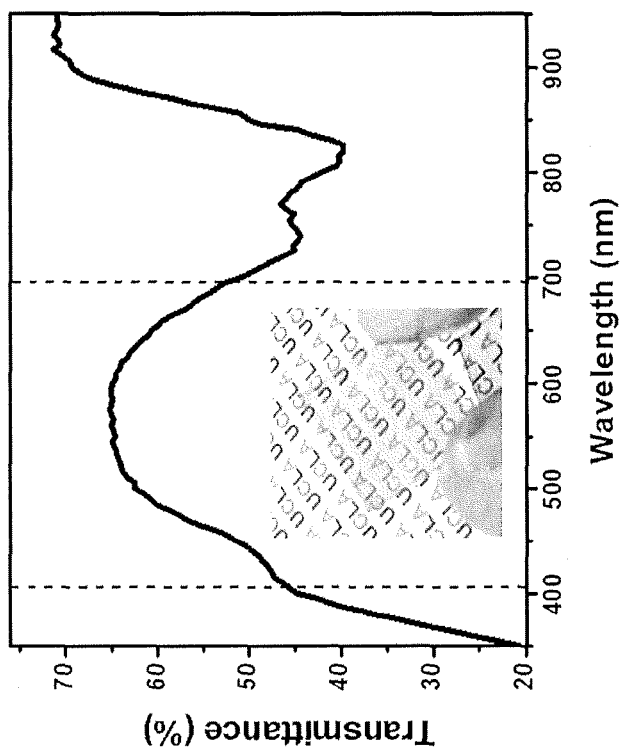

FIG. 10A shows the transmission spectrum and a photograph and FIG. 10B shows the current density-voltage characterization (illuminated from ITO side or AgNW composite electrode side) of the visibly-transparent PSC. The PCE of the best visibly-transparent PSC device was 4.4%, with an $V_{OC}$ of 0.72 V, a $J_{SC}$ of 11.3 mA/cm$^{-2}$, and a FF of 55%.

Example 6

Synthesis and Characterization of PBDTT-SeDPP

Figure 11A:
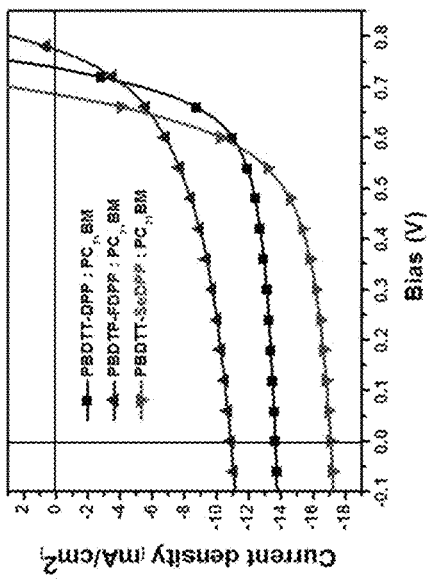
FIG. 11A shows chemical structures of PBDTT-FDPP, PBDTT-DPP and PBDTT-SeDPP.

The SeDPP monomer was synthesized using a reported method with slight modification (M. Shahid, et al, *Chem. Sci.* 2012, 3, 181). After adding the carbonitrile group onto the 2-position of selenophene, the SeDPP core unit was formed by condensation reaction with selenophene-2-carbonnitrile and diisopropylsuccinate in a basic environment. It should be noted that decreasing the reaction temperature (from 120° C. to 80° C.) and increasing the reaction time (from 2 hours to 12 hours) can enhance the yield of this step significantly, possibly due to the poor stability of the selenothiophene-2-carbonnitrile at high temperature. Then, 2-butyloctyl chains were attached onto the DPP core to ensure good solubility, and finally the bromination was performed by N-bromosuccinimide (NBS) under Argon protection. To fully investigate the effect of the Se-substitution on the DPP unit, the furan and thiophene counterparts (PBDTT-FDPP and PBDTT-DPP) were also synthesized and characterized for comparison, and their chemical structures are shown in FIG. 11A. The polymers PBDT-FDPP, PBDTT-DPP, and PBDTT-SeDPP were obtained via Stille-coupling polymerization. The gel permeation chromatography (GPC) measurements showed similar average molecular weights ($M_n$) of 35.2 kDa, 40.7 kDa, and 38.4 kDa for PBDTT-FDPP, PBDTT-DPP, and PBDTT-SeDPP, respectively. It should be noted that higher $M_n$ batches of PBDTT-DPP and PBDTT-SeDPP showed very poor solubility and cannot be used for solution processing. And higher $M_n$ batches of PBDTT-FDPP showed similar or even lower performance. For consistency, polymers with similar $M_n$ values were used. The polydispersity index of these three polymers was also determined by GPC to be around 2.1. These polymers were dissolved in chloroform (CF), chlorobenzene (CB), and dichlorobenzene (DCB).

Figure 11B:
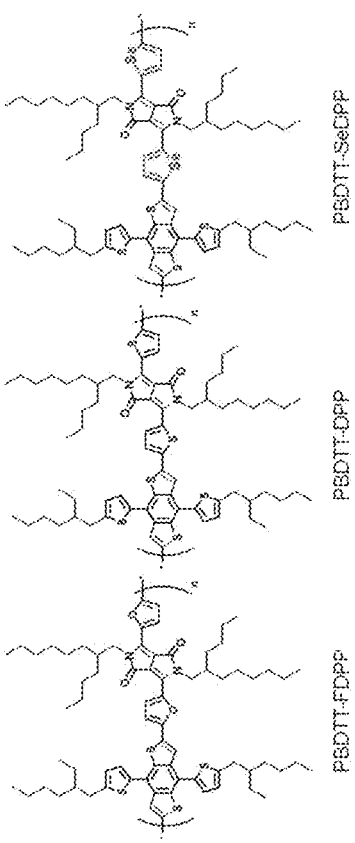
FIG. 11B shows absorption spectra of PBDTT-FDPP, PBDTT-DPP and PBDTT-SeDPP in thin films.

FIG. 11B shows the comparison of the ultraviolet/visible (UV/Vis) absorption spectra of the polymer thin films. All three polymers have a main absorption range starting from ~550, and the absorption edges are from 810 nm to 900 nm. The absorption shapes are similar to each other, which indicate the characteristics of the BDTT-DPP backbone system. The new PBDTT-SeDPP polymer displays a clear red-shift of the absorption onset as well as the maximum peak value (nearly 50 nm) as compared to PBDTT-DPP. According to the onset of the film absorption spectra, the optical bandgap of PBDT-FDPP, PBDTT-DPP, and PBDTT-SeDPP are calculated to be 1.51, 1.46, and 1.38 eV, respectively. The relatively low absorptivity in the visible region (400-650 nm) and high absorptivity in the NIR (650-900 nm) and UV (<400 nm) region of PBDTT-SeDPP make it a very promising candidate for high performance tandem PSCs and visibly-transparent PSC applications.

Example 7

Computational Studies

Figure 16:
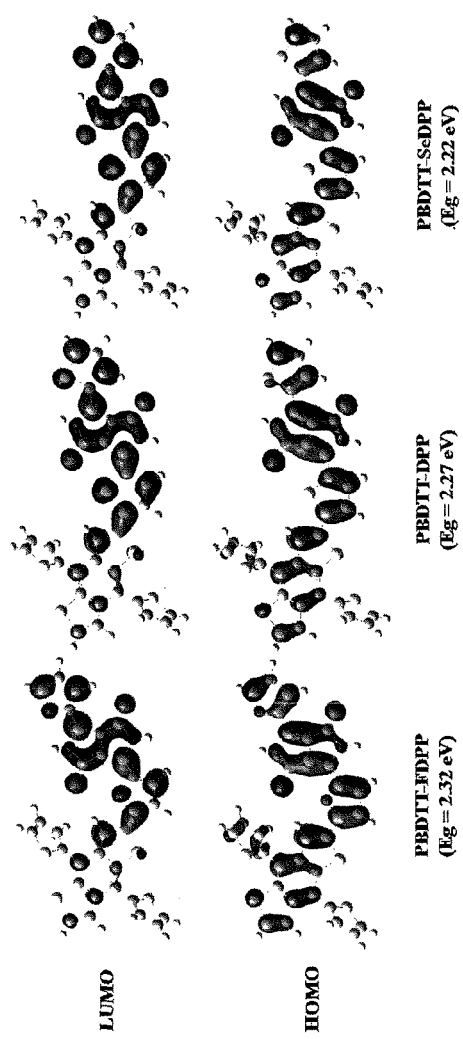
FIG. 16 shows calculated HOMOs and LUMOs of PBDTT-FDPP, PBDTT-DPP, and PBDTT-SeDPP.

To study the energy levels of this series of polymers, density functional theory (DFT) calculation was performed on one repeating unit (BDTT-FDPP, BDTT-DPP and BDTT-SeDPP) of the three polymers firstly and the calculated HOMO/LUMO are shown in FIG. 16. The result shows that by substituting the sulfur atoms with selenium atoms, the HOMO level increases slightly, and meanwhile the LUMO level drops a little. The narrowing of the bandgap is mainly due to the electron stabilizing effect of selenophene moieties, since selenium is more polarizable than either sulfur or oxygen. See a) A. J. Kronemeijier, E. Gili, M. Shahid, J. Pivnay, A. Salleo, M. Heeney, H. Sirringhaus, *Adv. Mater.* 2012, 24, 1558; b) J. S. Ha, K. H. Kim, D. H. Choi, *J. Am. Chem. Soc.* 2011, 133, 10364; c) M. Shahid, T. Mccarthy-Ward, J. Labram, S. Rossbauer, E. B. Domingo, S. E. Watkins, N. Stingelin, T. D. Anthopoulos, M. Heeney, *Chem. Sci.* 2012, 3, 181, each of which is incorporated by reference in its entirety.

The actual HOMO and LUMO energy levels of polymers are then determined by cyclic voltammetry (CV) measurement and the results from both DFT calculation and CV measurements are summarized in Table S1.

TABLE S1

Absorption properties and energy levels of the polymer thin films.

| | | | HOMO/LUMO (eV) | |
|---|---|---|---|---|
| | $\lambda_{max}/\lambda_{onset}$ (nm) | $Eg^{opt}$ (eV) | Calculated | CV |
| P1 | 757/810 | 1.51 | −4.90/−2.58 | −5.26/−3.64 |
| P2 | 769/852 | 1.46 | −5.00/−2.73 | −5.30/−3.63 |
| P3 | 808/900 | 1.38 | −4.98/−2.76 | −5.25/−3.70 |

P1: PBDTT-FDPP.
P2: PBDTT-DPP.
P3: PBDTT-SeDPP

Figure 18:
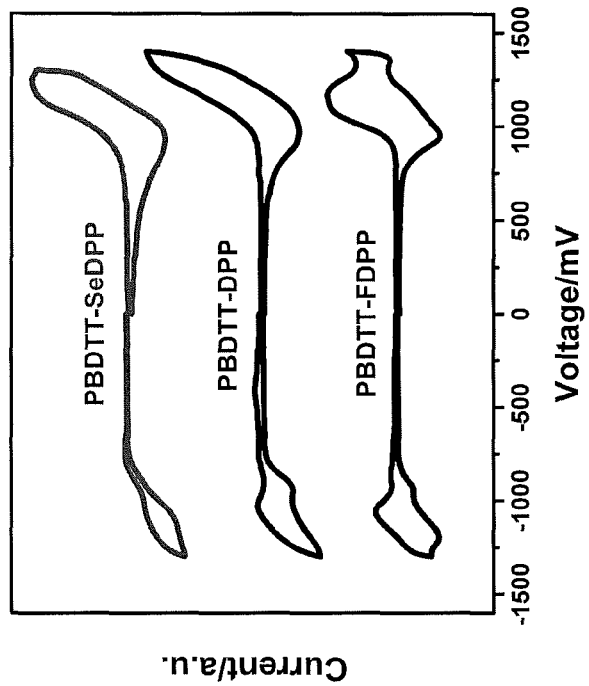
FIG. 18 shows cyclic voltammograms of polymer thin films.
Figure 17:
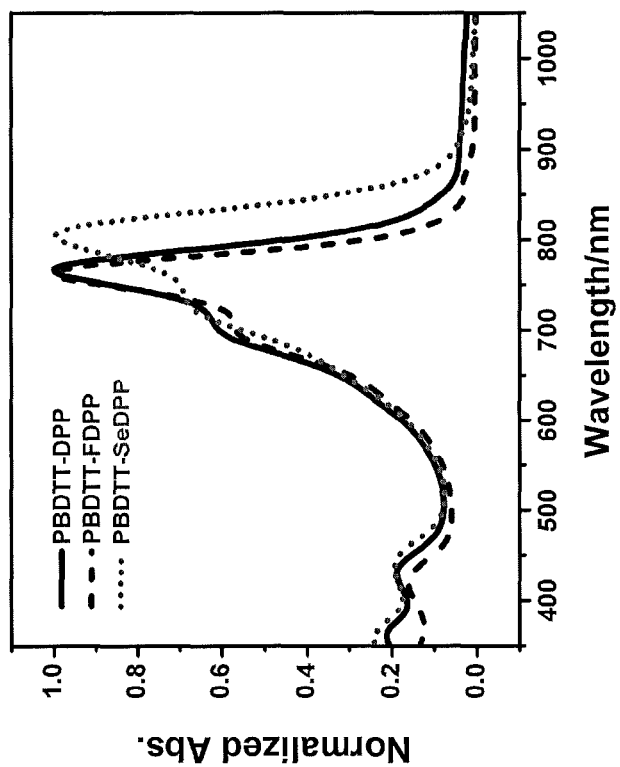
FIG. 17 UV/Vis absorption spectra of PBDTT-DPP, PBDTT-FDPP, and PBDTT-SeDPP dissolved in CHCl$_3$ (~0.1 mg/mL).

The HOMO/LUMO levels of PBDTT-FDPP, PBDTT-DPP, and PBDTT-SeDPP are measured to be −5.26/−3.64 eV, −5.30/−3.63 eV, and −5.25/−3.70 eV, respectively. The bandgap of PBDTT-FDPP turns out to be the smallest based on the CV testing, which conflicts with the optical bandgap; A similar phenomenon has also been observed in other FDPP based polymer systems. See e.g., C. H. Woo, P. M. Beaujuge, T. W. Holcombe, O. P. Lee, J. M. J. Fréchet, *J. Am. Chem. Soc.* 2010, 132, 15547, which is incorporated by reference in its entirety. Overall, the UV/Vis absorption spectra, DFT calculations, and the CV measurements are in good agreement. (UV/Vis absorption spectra of the polymers in solution and CV results can be found in FIGS. 17 and 18).

Example 8

Solar Cell Performance of PBDTT-SeDPP

Figure 12A:
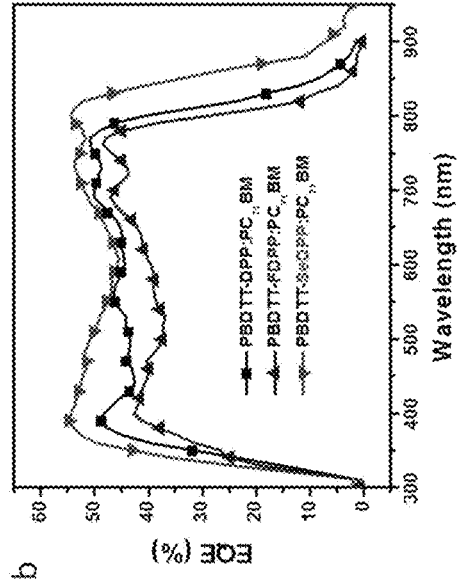
FIG. 12A shows current density-voltage characteristics of polymer/$PC_{71}BM$ single junction solar cellsunder AM1.5G illumination (100 $mW/cm^2$).
Figure 12B:
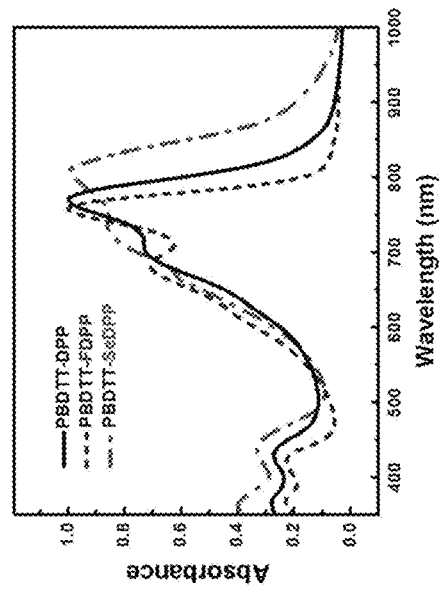
FIG. 12B shows EQEs of the corresponding devices.

Single junction BHJ solar cell performance of these polymers were investigated with the regular structure of ITO/PEDOT:PSS (30 nm)/polymer:PC71BM (100 nm)/Ca/Al under AM1.5G illumination (100 mW/cm2). These three polymers were spin-coated onto the PEDOT:PSS coated indium-doped tin oxide (ITO) glass substrate from DCB solution, followed by the evaporation of Ca/Al as top electrode. It should be noted that neither solvent nor thermal annealing was performed on all devices presented here, since no significant difference in the photovoltaic performance was observed for the annealed devices. The optimized polymer:PC$_{71}$BM ratio was found to be 1:2 by weight. Typical current density-voltage (J-V) curves are shown in FIG. 12A, the corresponding EQE curves are presented in FIG. 12B and the results are summarized in Table 1.

TABLE 1

Photovoltaic properties of single layer BHJ solar cells

| | $V_{OC}$ (V) | $J_{SC}$ (mA/cm$^2$) | FF (%) | PCE$_{max}$/$_{aver}$ (%) |
|---|---|---|---|---|
| P1 | 0.77 | 10.9 | 56 | 4.7/4.5 |
| P2 | 0.73 | 13.7 | 65 | 6.5/6.4 |
| P3 | 0.69 | 16.8 | 62 | 7.2/7.0 |

P1: PBDTT-FDPP.
P2: PBDTT-DPP.
P3: PBDTT-SeD

Figure 19:
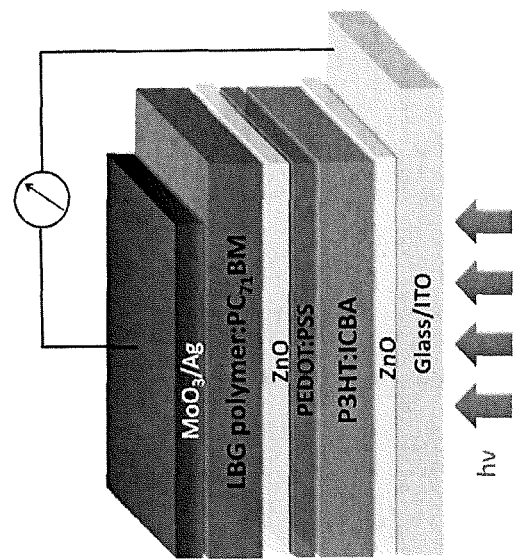
FIG. 19 shows Log J–Log(V–V$_{bi}$) characteristics of hole-only devices with structure of ITO/PEDOT:PSS/Polymers:PC$_{71}$BM/Au for PBDTT-DPP, PBDTT-FDPP, and PBDTT-SeDPP blended with PC$_{71}$BM (1:2, w:w).

As we can see, the $V_{OC}$ of the PSC drops from PBDTT-FDPP to PBDTT-DPP to PBDTT-SeDPP (from 0.77 to 0.73 to 0.69 V). The PBDTT-SeDPP based device turns out to have the lowest $V_{OC}$, and it is mainly due to a relatively high HOMO energy level. The $J_{SC}$, in contrast, increases from PBDTT-FDPP to PBDTT-DPP to PBDTT-SeDPP based devices. A high $J_{SC}$ of 16.8 mA/cm2 was observed in PBDTT-SeDPP based devices, which is 52% and 23% higher than PBDTT-FDPP (10.9 mA/cm$^2$) and PBDTT-DPP (13.7 mA/cm$^2$) based devices. With an FF of around 62%, the PBDTT-SeDPP based device shows a maximum efficiency of 7.2% (the averaged PCE from ~40 devices is 7.0%), whereas the PBDTT-FDPP and PBDTT-DPP based devices show max/average PCEs of 4.7/4.5% and 6.5/6.4%, respectively. From the EQE results (FIG. 12B), a broader coverage of PBDT-SeDPP from 300 nm to 900 nm is clearly seen. Also, the average values (note: estimated from numerical values between the two peaks at ~350 and ~800 nm) are around 42%, 47% and 53% for PBDTT-FDPP, PBDTT-DPP, and PBDTT-SeDPP based single-layer devices, respectively. The highest averaged EQE of the PBDTT-SeDPP based device is probably due to a slightly higher hole mobility of PBDTT-SeDPP ($6.9 \times 10^{-4}$ cm$^2$/V·s) as compared to that of PBDTT-DPP ($2.5 \times 10^{-4}$ cm$^2$/V·s) and PBDTT-FDPP ($2.2 \times 10^{-4}$ cm$^2$/V·s) in the blend film, which are determined by space charge limited current (SCLC) model (see FIG. 19). It worthy to note the maximum EQE for the LBG polymers (~50%) are still lower than the state-of-art MBG polymers such as PTB7 (~60%). See, e.g., a) H. Y. Chen, J. H. Hou, S. Q. Zhang, Y. Y. Liang, G. W. Yang, Y. Yang, L. P. Yu, Y. Wu, G. Li, Nat. Photon. 2009, 3, 649; b) Y. Y. Liang, Z. Xu, J. Xia, S. T. Tsai, Y. Wu, G. Li, C. Ray, L. P. Yu, Adv. Mater. 2010, 22, E135; c) Z. C. He, C. M. Zhong, X. Huang, W. Y. Wong, H. B. Wu, L. W. Chen, S. J. Su, Y. Cao, Adv. Mater. 2011, 23, 4636; d) C. M. Amb, S. Chen, K. R. Graham, J. Subbiah, C. E. Small, F. So, J. R. Reynolds, J. Am. Chem. Soc. 2011, 133, 10062; e) T. Y. Chu, J. P. Lu, S. Beaupre, Y. G. Zhang, J. R. Pouliot, S. Wakim, J. Y. Zhou, M. Leclerc, Z. Li, J. F. Ding, Y. Tao, J. Am. Chem. Soc. 2011, 133, 4250; f) L. J. Huo, S. Q. Zhang, X. Guo, F. Xu, Y. F. Li, J. H. Hou, Angew. Chem. Int. Ed. 2011, 50, 1, each of which is incorporated by reference in its entirety. One possible reason provided by Janssen is that the relatively low-lying LUMO levels of the LBG polymers led to poor charge separation and thus low internal quantum efficiency (IQE) of the devices. (W. W. Li, W. S. C. Roelofs, M. M. Wienk, R. A. J. Janssen, J. Am. Chem. Soc. 2012, 134, 13787, which is incorporated by reference in its entirety). Here the IQE of PBDTT-SeDPP based devices was around 60%, indicating there is still significant energy loss during the photon-to-electron conversion process. Further optimizing the energy levels of the materials as well photo-physics study to understand the mechanism are currently underway.

The morphology of the blend films, which is believed to be critical for the efficient charge transport in the polymer domains and charge separation at the polymer/fullerene interfaces,[1,7] was examined by transmission electron microscopy (TEM) and the results are shown in FIG. 13. It is found that both PBDTT-DPP:PC$_{71}$BM and PBDTT-SeDPP:PC$_{71}$BM blend films show fine features of phase separation and plausibly bi-continuous networks (FIGS. 13b, 13c) whereas the PBDTT-FDPP:PC$_{71}$BM blend film shows slightly weaker phase separation (FIG. 13a). The more favorable morphology of PBDTT-DPP:PC$_{71}$BM and PBDTT-SeDPP:PC$_{71}$BM blend films may contribute to the high performance of these two polymers. It should be pointed out that these morphology features were developed spotaneously since as-cast films were used during the processing. In addition, previous research on the morphology optimization of PBDTT-FDPP has led to slightly enhanced PCE (up to 5.8%) by using 1,8-diiodooctane (DIO) as additive during device processing. However, no improvement of the performance of PBDTT-DPP was observed using DIO as additive and similar results are obtained here for the new polymer PBDTT-SeDPP. The broader absorption range and higher EQE in the whole region of PBDTT-SeDPP compared to its furan or thiophene counterparts lead to the significant enhancement of $J_{SC}$ of PBDTT-SeDPP based devices. Further studies on the structural order and molecular packing will be carried out to fully understand this enhancement. Although the devices containing the Se-substituted polymer show a slightly lower $V_{OC}$ due to its higher HOMO level, the overall performance was improved due to the significant enhancement of the $J_{SC}$.

Example 9

Tandem and Visibly Transparent Solar Cells Incorporating PBDTT-SeDPP

The versatile photovoltaic applications of PBDTT-SeDPP are featured by tandem and visibly-transparent PSCs. The tandem solar cell architecture, which consists of a front cell with a wide-bandgap material, an interconnecting layer (ICL), and a rear cell with a LBG material, is an effective way to harvest a broader part of the solar spectrum and make more efficient use of the photonic energy than the single junction structure.[4] Tandem PSCs with inverted configuration[4d,12] were fabricated using PBDTT-SeDPP as the rear cell donor material. P3HT (Eg ~1.9 eV) was used as the front cell donor material and indeneC$_{60}$ bisadduct (IC$_{60}$BA) [13] was used as the front cell acceptor material. The device structure is ITO/ZnO (30 nm)/P3HT:IC60BA (160 nm)/PEDOT:PSS (30 nm)/ZnO (30 nm)/PBDTT-SeDPP:PC$_{71}$BM (100 nm)/MoO$_3$ (5 nm)/Ag (shown in FIG. 20). FIG. 14a shows the J-V characteristics of a typical inverted single junction front cell device, rear cell device, and the inverted tandem device. The averaged PCE from 20 tandem devices is 9.5% with a VOC of 1.52 V, a JSC of 9.44 mA/cm2, and a FF of 66.3%. The $V_{OC}$ of the tandem device is almost the sum of two sub-cells (0.84 V and 0.69 V), indicating the effectiveness of the highly performing ICL. The FF of the tandem device is around the average of the two sub-cells (70% for the front cell and 62% for the rear cell). The major improvement compared to previously reported tandem cells based on PBDTT-DPP is the $J_{SC}$ (from ~8.3 A/cm$^2$ to 9.4 A/cm$^2$). To further confirm the high $J_{SC}$ achieved here, EQE of the two sub-cells in the tandem device was measured using a reported method. [4g, 14] As shown in FIG. 14b, the front cell had a photo-response from 300 to 650 nm, showed an EQE as high as 67% at 530 nm, and its integrated $J_{SC}$ was 9.3 mA/cm². The rear cell had a broad photo-response from 300 to 900 nm, showed a maximum EQE of 51% at 810 nm, and a balanced integrated JSC of 9.2 mA/cm² was achieved. The high $J_{SC}$ obtained from the rear cell is due to the ability of PBDTT-SeDPP to use the NIR light very efficiently.

Figure 15:
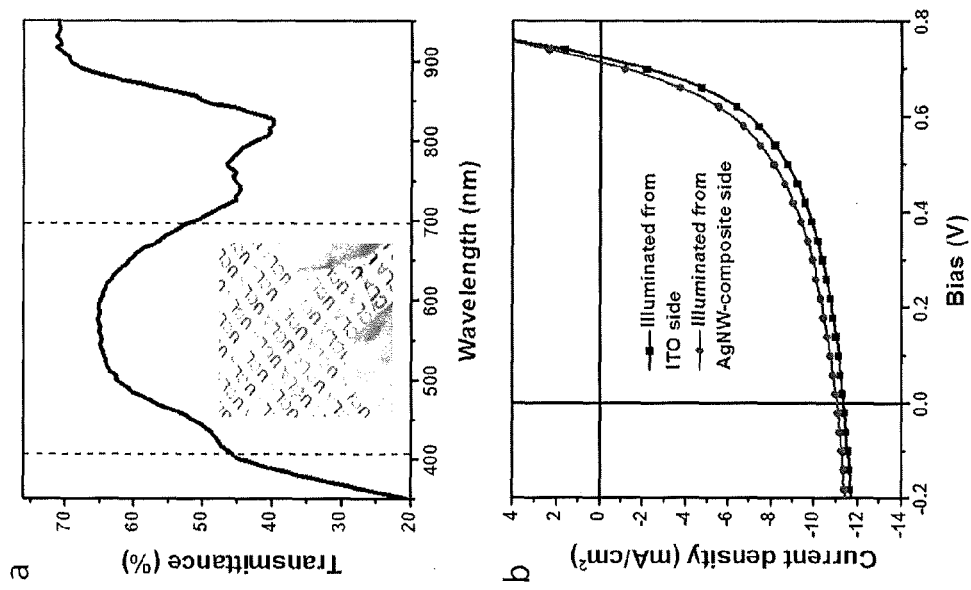
FIG. 15 shows (a) Transmission spectrum and a photograph, (b) Current density-voltage characterization (illuminated from ITO side or AgNW composite electrode side) of the visibly-transparent polymer solar cell with the device structure of ITO/PEDOT:PSS/PBDTT-SeDPP:PC$_{61}$BM/TiO$_2$/AgNW.
Figure 21:
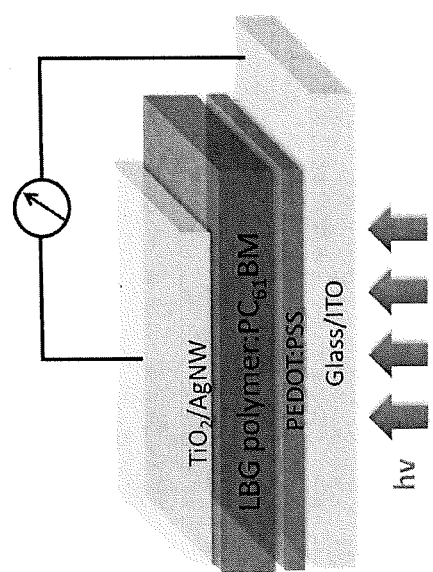
FIG. 21 shows a device structure of a visibly-transparent polymer solar cell.

The visibly-transparent PSC, which enables part of the visible light (400-700 nm) passing through the device, has high potential in many photovoltaic applications, such as building-integrated photovoltaics (BIPV) or integrated photovoltaic-chargers for portable electronics.[5,12] Previous studies showed ether low transmittance in the visible region or low efficiencies due to the lack of a proper LBG polymer that can use the NIR light very efficiently while transmit most of the visible light.[5a-5e,12] Recently, we have demonstrated a visibly-transparent PSC with PCE of 4% and transmittance ~60% by using PBDTT-DPP as the active material.[5f] The performance was limited mainly by the relatively narrow absorption range (up to 850 nm) and low external quantum efficiency (<50%) in the NIR region. Here, a highly efficient visibly-transparent PSC is demonstrated with the device structure of ITO/PEDOT:PSS (30 nm)/PBDTT-SeDPP:PC$_{61}$BM (100 nm)/TiO2/AgNW and a schematic structure is shown in FIG. 21. It should be noted that the high-performance AgNW-based composite transparent electrode plays an important role and the detailed preparation and characterization of it can be found in reference 5f. FIG. 15a shows the transmission spectrum and a photograph of the complete device. It can be found that an average light transmission of 58% within the 400 to 700 nm range and a maximum transmission of 66% at ~550 nm are achieved. From the real device image, the UCLA logo with different colors can be seen clearly. FIG. 15b demonstrates the J-V curves of the visibly-transparent PSC. The device performance was measured with illumination from either the ITO substrate side or the top AgNW-composite transparent conductor side. When illuminated from the ITO substrate side, a PCE of 4.5% was achieved with Voc=0.72 V, Jsc=11.5 mA·cm-2, and FF=55%. Ref 5f showed PBDTT-DPP based visibly-transparent OPV with PCE of 3.9%. The transmission spectrum in the visible region is similar in the two visibly transparent OPV devices. The 15% improvement in efficiency clearly shows that harvesting NIR photons by the new polymer is more effective in the visibly-transparent solar cells. When the device test was performed with illumination from the top AgNW composite electrode side, similar performance was obtained: Voc=0.71 V, Jsc=11.2 mA·cm-2, FF=54%, and PCE=4.3%. The difference of the $J_{SC}$ is due to the slightly lower transparency of the AgNW-based composite electrode films as compared to the commercial ITO substrates.[5f] These results show that with effective NIR photon harvesting and proper energy levels, PBDTT-SeDPP is a good candidate for visibly-transparent PSCs with real world applications.

Design, synthesis, and characterization of a selenium-substituted LBG polymer PBDTT-SeDPP has been described. The substitution of the O or S by Se atoms on the DPP unit led to a reduced bandgap and enhanced hole mobility of the polymers. High photo-current of 16.8 mA/cm² and PCE of 7.2% were obtained in a single junction PSC device, which showed significant improvement compared to its counterparts PBDTT-FDPP and PBDTT-DPP. Even more importantly, the new polymer significantly enhanced the tandem and visibly-transparent PSCs performance, with PCEs as high as 9.5% and 4.5%, respectively. Our result is an excellent example of the selenium-substitution approach to improve the photovoltaic performance of LBG polymers.

EXPERIMENTAL

Materials:

2,6-Bis(trimethyltin)-4,8-bis(5-ethylhexyl-2-thienyl)-benzo[1,2-b:4,5-b']dithiophene (BDTT), 2,5-Diethylhexyl-3,6-bis(5-bromofuran-2-yl)pyrrolo[3,4-c]-pyrrole-1,4-dione (FDPP), 2,5-Dibutyloctyl-3,6-bis(5-bromothiophen-2-yl) pyrrolo[3,4-c]-pyrrole-1,4-dione (DPP), Selenophene-2-carbonitrile, 2-ethylhexylthiophene and Indene-C$_{60}$bisadduct (ICBA) were synthesized according to the procedures reported in the literature (Dou, L., et al., *J. Am. Chem. Soc.* 2012, 134, 10071; Woo, C. H., et al., *J. Am. Chem. Soc.* 2010, 132, 15547; and Shahid, M., et al., *Chem. Sci.* 2012, 3, 181, each of which is incorporated by reference in its entirety). Poly(3-hexylthiophene) (P3HT) was purchased from Rieke Metals. [6,6]-phenyl-C$_{71}$-butyric acid methyl ester (PC$_{71}$BM) was purchased from Nano-C. Diisopropylsuccinate was purchased from TCI. Unless otherwise stated, all of the chemicals were purchased from Aldrich and used as received. The polymers are polymerized by Stille coupling of different monomers. See supporting information for more synthetic details.

Fabrication of Regular Structure Single Cell:

PBDTT-FDPP, PBDTT-DPP or PBDTP-SeDPP was co-dissolved with PC$_{71}$BM in 1,2-dichlorobenzene (DCB) with a weight ratio of 1:2 with a polymer concentration of 8 mg/mL. ITO-coated glass substrates (15 Ω/cm²) were cleaned stepwise in detergent, water, acetone, and isopropyl alcohol under ultrasonication for 15 min each and subsequently dried in an oven for 5 h. A thin layer (~30 nm) of PEDOT:PSS (Baytron P VP A1 4083) was spin-coated onto the ITO surface which was pretreated by ultraviolet ozone for 15 min. Low-conductivity PEDOT:PSS was chosen to minimize measurement error from device area due to lateral conductivity of PEDOT:PSS. After being baked at 120° C. for ~20 min, the substrates were transferred into a nitrogen-filled glove box (<0.1 ppm O$_2$ and H$_2$O). A polymer/PC$_{71}$BM composite layer (ca. 100 nm thick) was then spin-cast from the blend solutions at 2500 rpm on the ITO/PEDOT:PSS substrate without any annealing or other special treatments. Then the film was transferred into a thermal evaporator that is located in the same glovebox. A Ca layer (20 nm) and an Al layer (100 nm) were deposited in sequence under a vacuum of 2×10⁻⁶ torr. The effective area of the device was measured to be 0.10 cm². See supporting information for more device fabrication and characterization details.

Scheme S1. Synthesis of monomers, PBDTT—FDPP, PBDTT—DPP, and PBDTT—SeDPP

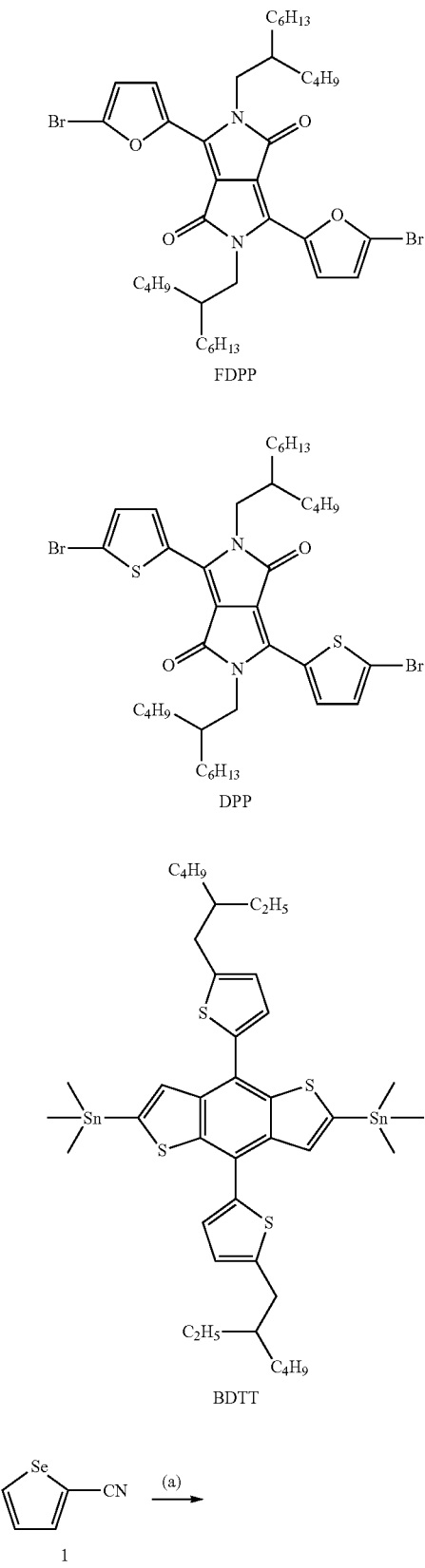

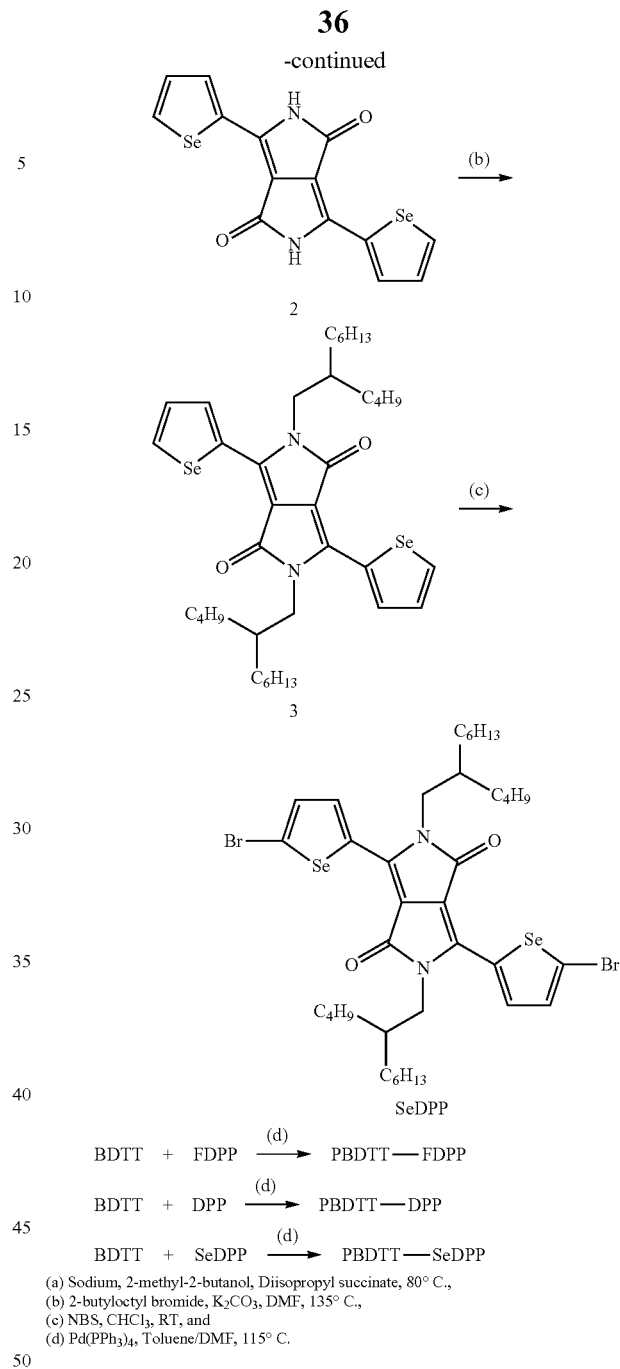

BDTT + FDPP —(d)→ PBDTT—FDPP
BDTT + DPP —(d)→ PBDTT—DPP
BDTT + SeDPP —(d)→ PBDTT—SeDPP (a) Sodium, 2-methyl-2-butanol, Diisopropyl succinate, 80° C.,
(b) 2-butyloctyl bromide, $K_2CO_3$, DMF, 135° C.,
(c) NBS, $CHCl_3$, RT, and
(d) Pd(PPh$_3$)$_4$, Toluene/DMF, 115° C.

Materials 2,6-Bis(trimethyltin)-4,8-bis(5-ethylhexyl-2-thienyl)-benzo[1,2-b:4,5-b']dithiophene (BDTT), 2,5-Diethylhexyl-3,6-bis(5-bromofuran-2-yl)pyrrolo[3,4-c]-pyrrole-1,4-dione (FDPP), 2,5-Dibutyloctyl-3,6-bis(5-bromothiophen-2-yl)pyrrolo[3,4-c]-pyrrole-1,4-dione (DPP), Selenophene-2-carbonitrile (1), 2-ethylhexylthiophene and Indene-$C_{60}$bisadduct (ICBA) were synthesized according to the procedures reported in the literature. Poly(3-hexylthiophene) (P3HT) was purchased from Rieke Metals. [6,6]-phenyl-$C_{71}$-butyric acid methyl ester (PC$_{71}$BM) was purchased from Nano-C. Diisopropyl succinate was purchased from TCI. Unless otherwise stated, all of the chemicals were purchased from Aldrich and used as received.

3,6-Dithiophen-2-yl-2,5-dihydropyrrolo[3,4-c]pyrrole-1,4-dione (2)

Sodium (1.54 g, 67.2 mmol) was added to a two-neck round bottom flask with nitrogen protection. 2-methyl-2-butanol (38 mL) was subsequently added, and followed by heating up the solution to 110° C. until the sodium was totally consumed. After cooled down the solution to 65° C., the compound 1 (7.0 g, 44.9 mmol) was injected in one portion. The mixture was stirred for another 20 min, and then diisopropyl succinate (3.94 g, 19.5 mmol) was slowly dropped in 1 h. The reaction temperature was gradually increased to 70° C. and kept for about 1 h. Then the solution was further heated to 80° C. and stirred for an additional 11 h. Finally, the mixture was cooled to 0° C., diluted with 20 mL methanol, and neutralized by stirring with acetic acid. After 2 h, the suspension was filtered, and the black filter cake was washed with methanol and water twice and dried in vacuum to obtain a dark purple crude product that could be used directly without further purification (6.2 g, yield 81%).

2,5-Di(2-octyldodecyl)-3,6-bis-(selenophenyl)-1,4-diketopyrrolo[3,4c]pyrrole (3)

Compound 2 (2.9 g, 7.4 mmol), 18-crown-6 (~20 mg), and anhydrous potassium carbonate (4.57 g, 33.1 mmol) were dissolved into N,N-dimethylformamide (50 ml) in a two-neck round flask under nitrogen protection. 2-butyloctyl bromide (7.3 g, 29.4 mmol) was injected in one portion by syringe, and gradually heated to 120° C. After 4 h, the reaction was further heated to 135° C. with stirring for another 8 h. The reaction mixture was the cooled to room temperature, poured into 100 mL of ice water and extracted with dichloromethane. The combined extracts were washed with water several times, and the solvent was then removed under reduced pressure. After drying, the crude product was purified by silica gel chromatography using a dichloromethane and hexane mixture as the eluent to obtain a purple-red solid (1.1 g, 20%). 1H NMR (CDCl3, 400 MHz): 8.79 (d, 2H), 8.37 (d, 2H), 7.47 (m, 2H), 3.96 (d, 4H), 1.91 (br, 2H), 1.55-0.83 (br, 44H).

2,5-Di(2-octyldodecyl)-3,6-bis-(5-bromoselenophenyl)-1,4-diketopyrrolo[3,4c]pyrrole (SeDPP)

Compound 3 (0.74 g, 1.0 mmol) and N-bromosuccinimide (0.38 g, 2.1 mmol) were dissolved into chloroform (20 mL) in a two-neck round bottom flask under nitrogen protection, then the reaction mixture was protected from light and stirred at room temperature overnight. The mixture was then poured into methanol (100 mL) and then filtered. The filtered cake was washed with hot water and methanol twice. After drying in a vacuum, the pure product was obtained as dark-purple solid (0.7 g, 78%). $^1$H NMR (CDCl$_3$, 400 MHz): 8.38 (d, 2H), 7.39 (d, 2H), 3.86 (d, 4H), 1.89 (br, 2H), 1.40-0.80 (br, 44H).

Polymerization for PBDTT-SeDPP

SeDPP (0.1760 g, 0.1981 mmol) and compound BDTT (0.1810 g, 0.2001 mmol) were dissolved into 10 mL toluene and 1 mL DMF in a flask protected by argon. The solution was flushed with argon for 10 minutes, then 10 mg of Pd(PPh$_3$)$_4$ was added into the flask. The solution was flushed with argon again for another 10 minutes. The oil bath was heated to 115° C. gradually, and the reaction mixture was stirred for 8 hours at 115° C. under argon atmosphere. Then, the mixture was cooled down to room temperature and the polymer was precipitated in 100 ml methanol and the precipitated solid was collected and purified by silica gel chromatography using chloroform as eluent. The polymer was obtained as dark green-purple solid, yield 56%. The polymer can be readily dissolved into chloroform, chlorobenzene or dichlorobenzene, etc. $^1$H NMR (400 MHz, CDCl$_3$): δ=6.4-9.0 (br, 10H), 2.5-4.0 (br, 12H), 0.6-1.6 (br, 72H). Mn=38.0 k; polydispersity=2.1.

Polymerization for PBDTT-FDPP

PBDTT-FDPP was prepared using the same procedure as PBDTT-SeDPP. $^1$H NMR (400 MHz, CDCl$_3$): 6.4-8.6 (br, 10H), 1.8-4.2 (br, 12H), 0.6-1.5 (br, 72H). Mn=35.2 k; polydispersity=2.2.

Polymerization for PBDTT-DPP

PBDTT-DPP was prepared using the same procedure as PBDTT-SeDPP. $^1$H NMR (400 MHz, CDCl$_3$): 6.7-8.6 (br, 10H), 1.8-4.9 (br, 12H), 0.6-1.5 (br, 72H). Mn=40.3 k; polydispersity=2.2.

Computational Calculation

The geometry of all three compounds was subjected to density functional theory (DFT) optimizations by Gaussian 03 software package. Hybrid three-parameter B3LYP functional combined with 6-31G(d) basis set was used. The HOMO as well as LUMO energy levels were analyzed using minimized singlet geometries to approximate the ground state.

Materials Characterization

Instrumentation $^1$H and $^{13}$C NMR spectra were measured on a Bruker ARX-400 spectrometer. Absorption spectra were taken on a Varian Cary 50 ultraviolet-visible spectrometer. Gel permeation chromatographic analysis (GPC) was performed on a Varian Star Chromatography Workstation (column: MIXED-C from Polymer Laboratories) connected with one UV/Vis detector from Varian (ProStar 340). All GPC analyses were performed on polymer/chloroform solution at the flow rate of 1 ml/min at 40° C. and calibrated with polystyrene. The electrochemical cyclic voltammetry (CV) was conducted with Pt disk, Pt plate, and Ag/AgCl electrode as working electrode, counter electrode, and reference electrode, respectively, in a 0.1 mol/L tetrabutylammoniumhexafluorophosphate (Bu$_4$NPF$_6$) acetonitrile solution. The polymer films for electrochemical measurements were coated from a polymer chloroform solution, ca. 5 mg/mL. For calibration, the redox potential of ferrocene/ferrocenium (Fc/Fc$^+$) was measured under the same conditions, and it is located at 0.39 V vs. the Ag/AgCl electrode. It is assumed that the redox potential of Fc/Fc$^+$ has an absolute energy level of −4.80 eV to vacuum. The energy levels of the HOMO and LUMO were then calculated according to the following equations $$E_{HOMO}=-(\phi_{ox}+4.41) \text{ (eV)}$$

$$E_{LUMO}=-(\phi_{re}+4.41) \text{ (eV)}$$

Where $\phi_{ox}$ is the onset oxidation potential vs Ag/AgCl and $\phi_{re}$ is the onset reduction potential vs Ag/AgCl.

Device Fabrication and Measurement

Regular Structure Single Cell

PBDTT-FDPP, PBDTT-DPP or PBDTP-SeDPP was co-dissolved with $PC_{71}BM$ in 1,2-dichlorobenzene (DCB) with a weight ratio of 1:2 with a polymer concentration of 8 mg/mL. ITO-coated glass substrates (15 $\Omega/cm^2$) were cleaned stepwise in detergent, water, acetone, and isopropyl alcohol under ultrasonication for 15 min each and subsequently dried in an oven for 5 h. A thin layer (~30 nm) of PEDOT:PSS (Baytron P VP A1 4083) was spin-coated onto the ITO surface which was pretreated by ultraviolet ozone for 15 min. Low-conductivity PEDOT:PSS was chosen to minimize measurement error from device area due to lateral conductivity of PEDOT:PSS. After being baked at 120° C. for ~20 min, the substrates were transferred into a nitrogen-filled glove box (<0.1 ppm $O_2$ and $H_2O$). A polymer/$PC_{71}BM$ composite layer (ca. 100 nm thick) was then spin-cast from the blend solutions at 2500 rpm on the ITO/PEDOT:PSS substrate without any annealing or other special treatments. Then the film was transferred into a thermal evaporator that is located in the same glovebox. A Ca layer (20 nm) and an Al layer (100 nm) were deposited in sequence under a vacuum of $2\times10^{-6}$ torr. The effective area of the device was measured to be 0.10 $cm^2$.

Inverted Tandem Cells

Figure 20:
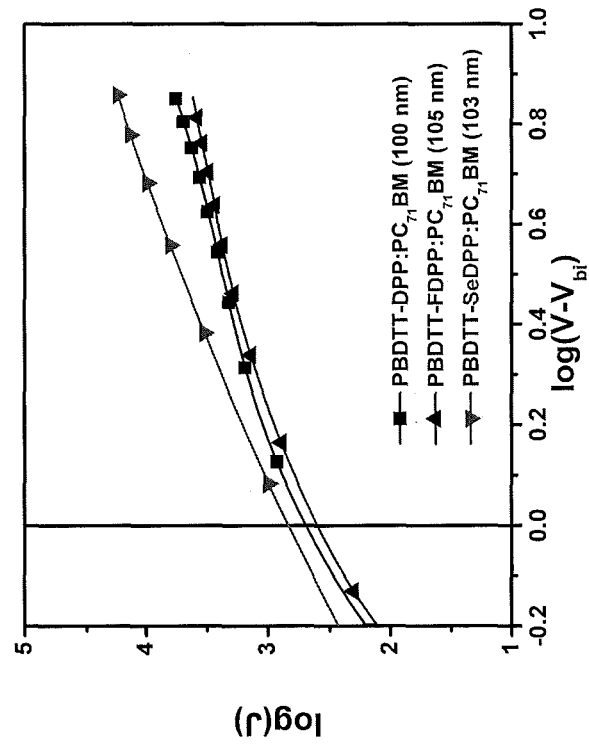
FIG. 20 shows a device structure of an inverted tandem solar cell.

The device architecture of the tandem solar cell is shown in FIG. 20. The pre-cleaned ITO substrates were treated with UV-ozone. The P3HT:ICBA at a 1:1 weight ratio in DCB with a 18 mg/mL polymer concentration was spin-casted at 800 rpm for 30 on top of a layer of ZnO. The Films were annealed at 150° C. for 10 min. PEDOT:PSS was spin-coated on the first active layer, and annealed at 150° C. for 10 min. After that, a thin layer of ZnO film was spin-cast, followed by thermal annealing at 150° C. for 10 min. Polymer:$PC_{71}BM$ at a 1:2 weight ratio in DCB with a 8 mg/mL polymer concentration was then spin-coated without any subsequent processing. The device fabrication was completed by thermal evaporation of 15 nm $MoO_3$ and 100 nm Ag as the anode under vacuum at a base pressure of $2\times10^{-6}$ torr. The effective area of the device was measured to be 0.10 $cm^2$.

Visibly-Transparent Solar Cells

Visibly transparent PSCs were fabricated on patterned ITO-coated glass substrates. The PEDOT:PSS layer was spin-cast at 4000 rpm for 60 s and annealed at 120° C. for 15 min in air. The PBDTT-SeDPP:PCBM at a weight ratio of 1:2 in DCB with a 8 mg/mL polymer concentration was spin-cast at 2500 rpm for 80 s on top of the PEDOT:PSS layer to form a ~100 nm thick active layer. A $TiO_2$ sol-gel solution was then spin-coated onto the active layer at 2500 rpm for 30 s and annealed at 100° C. for 1 min to form the n-type interface layer. For the deposition of the AgNW-based composite electrode, the silver nanowire dispersion in isopropyl alcohol was spin-coated (2 mg/mL dispersion, 2500 rpm, 10 drops) onto the $TiO_2$ layer to form AgNW conducting networks. The fusing process of the silver nanowire network was then carried out by applying diluted $TiO_2$ sol-gel solution in ethanol at 3000 rpm and baking at 100° C. for 10 s. The ITO nanoparticle dispersion (10 wt %) was used as transparent conductive filler and was spin-coated onto the fused AgNW matrix to form the composite electrode. Mild heating at 80° C. for 1 min removed the residual solvent. The thickness of the transparent composite electrode is around 400 nm. The device electrode fingers were formed by cutting the films with a blade and blowing the devices with $N_2$ to avoid possible short circuits between the top AgNWs and the bottom ITO substrate. The active area is 0.10 $cm^2$, which is defined by the overlap between bottom ITO substrate and the top fingers.

Current-Voltage Measurement

The fabricated device was encapsulated in a nitrogen-filled glovebox by UV cured epoxy and a cover glass. The J-V curves were measured using a Keithley 2400 source-measurement unit. The photocurrent was measured under AM 1.5 G illumination at 100 $mW/cm^2$ under a Newport Thermal Oriel 91192 1000W solar simulator. The light intensity was determined by a Si photodiode as a reference cell, followed by the calculation of spectral mismatch factor and then $J_{SC}$ correction. EQEs were measured using a lock-in amplifier (SR830, Stanford Research Systems) with current preamplifier (SR570, Stanford ResearchSystems) under short-circuit conditions. The devices were illuminated by monochromatic light from a xenon lamp passing through a monochromator (SpectraPro-2150i, Acton Research Corporation) with a typical intensity of 10 μW. The photocurrent signal is then amplified by an SR570 and detected with an SR830. A calibrated monosilicon diode with known spectral response is used as a reference.

Hole Mobility

Hole mobility was measured using the space charge limited current model (SCLC), using a diode configuration of ITO/PEDOT:PSS/polymer:$PC_{71}BM$/Au and taking current-voltage measurements in the range of 0-10 V and fitting the results to a space charge limited form, where the SCLC is described by $$J=(8/9)\epsilon_r\epsilon_0\mu_e(V^2/L^3)$$

where $\epsilon_0$ is the permittivity of free space, $\epsilon_r$ is the dielectric constant of the polymer, μ is the hole mobility, V is the voltage drop across the device ($V=V_{appl}-V_r-V_{bi}$, where $V_{appl}$ is the applied voltage to the device, $V_r$ is the voltage drop due to contact resistance and series resistance across the electrodes, and $V_{bi}$ is the built-in voltage due to the difference in work function of the two electrodes), L is the polymer thickness. The dielectric constant $\epsilon_r$ is assumed to be 3, which is a typical value for conjugated polymers. The thickness of the polymer films is measured by using a Dektak profilometer.

Transmission Electron Microscopy Measurements

Transmission electron microscopy was conducted with a JEOL 2010F electron microscope.

REFERENCES

[1] a) G. Yu, J. Gao, J. C. Hummelen, F. Wudl, A. J. Heeger, *Science* 1995, 270, 1789; b) G. Li, V. Shrotriya, J. S. Huang, Y. Yao, T. Moriarty, K. Emery, Y. Yang, *Nat. Mater.* 2005, 4, 864; c) F. C. Krebs, *Sol. Energy Mater. Sol. Cells* 2009, 93, 394; d) J. Brabec, N. S. Sariciftci, J. C. Hummelen, *Adv. Funct. Mater.* 2011, 11, 15; e) G. Li, R. Zhu, Y. Yang, *Nat. Photon.* 2012, 6, 153.

[2] a) B. C. Thompson, J. M. J. Frechet, *Angew. Chem. Int. Ed.* 2008, 47, 58; b) Y. J. Cheng, S. H. Yang, C. S. Hsu, *Chem. Rev.* 2009, 109, 5868; c) P. L. T. Boudreault, A. Najari, M. Leclerc, *Chem. Mater.* 2011, 23, 456; d) P. M. Beaujuge, J. M. J. Frechet, *J. Am. Chem. Soc.* 2011, 133, 20009.

[3] W. Shockley, H. J. Queisser, *J. Appl. Phys.* 1961, 32, 510.

[4] a) A. Hadipour, B. de Boer, J. Wildeman, F. B. Kooistra, J. C. Hummelen, M. G. R. Turbiez, M. M. Wienk, R. A. J. Janssen, P. W. M. Blom, *Adv. Funct. Mater.* 2006, 16, 1897; b) J. Y. Kim, K. Lee, N. E. Coates, D. Moses, T. Q. Nguyen, M. Dante, A. J. Heeger, *Science* 2007, 317, 222; c) S. Sista, M. H. Park, Z. R. Hong, Y. Wu, J. H. Hou, W. L. Kwan, G. Li, Y. Yang, *Adv. Mater.* 2010, 22, 380; d) C. H. Chou, W. L. Kwan, Z. R. Hong, L. M. Chen, Y. Yang, *Adv. Mater.* 2011, 23, 1282; e) J. Yang, R. Zhu, Z. Hong, A. Kumar, Y. Yang, *Adv. Mater.* 2011, 23, 3465; f) V. S. Gevaerts, A. Furlan, M. M. Wienk, M. Turbiez, R. A. J. Janssen, *Adv. Mater.* 2012, 24, 2130; g) L. T. Dou, J. B. You, J. Yang, C.-C. Chen, Y. J. He, S. Murase, T. Moriarty, K. Emery, G. Li, Y. Yang, *Nat. Photon.* 2012, 6, 180.

[5] a) R. F. Bailey-Salzman, B. P. Rand, S. R. Forrest, *Appl. Phys. Lett.* 2006, 88, 233502; b) G. M. Ng, L. K. Elizabeth, T. Kietzke, L. W. Tan, P. K. Liew, F. R. Zhu, *Appl. Phys. Lett.* 2007, 90, 103505; c) J. S. Huang, G. Li, Y. Yang, *Adv. Mater.* 2008, 20, 415-419; d) W. Gaynor, J. Y. Lee, P. Peumans, *ACS Nano* 2010, 4, 30-34; e) J. Meiss, F. Holzmueller, R. Gresser, K. Leo, M. Riede, *Appl. Phys. Lett.* 2011, 99, 193307; f) C.-C. Chen, L. T. Dou, R. Zhu, C.-H. Chung, T.-B. Song, Y. B. Zheng, S. Hawks, G. Li, P. S. Weiss, Y. Yang, *ACS Nano* 2012, 6, 7185.

[6] a) H. Y. Chen, J. H. Hou, S. Q. Zhang, Y. Y. Liang, G. W. Yang, Y. Yang, L. P. Yu, Y. Wu, G. Li, *Nat. Photon.* 2009, 3, 649; b) Y. Y. Liang, Z. Xu, J. Xia, S. T. Tsai, Y. Wu, G. Li, C. Ray, L. P. Yu, *Adv. Mater.* 2010, 22, E135; c) Z. C. He, C. M. Zhong, X. Huang, W. Y. Wong, H. B. Wu, L. W. Chen, S. J. Su, Y. Cao, *Adv. Mater.* 2011, 23, 4636; d) C. M. Amb, S. Chen, K. R. Graham, J. Subbiah, C. E. Small, F. So, J. R. Reynolds, *J. Am. Chem. Soc.* 2011, 133, 10062; e) T. Y. Chu, J. P. Lu, S. Beaupre, Y. G. Zhang, J. R. Pouliot, S. Wakim, J. Y. Zhou, M. Leclerc, Z. Li, J. F. Ding, Y. Tao, *J. Am. Chem. Soc.* 2011, 133, 4250; f) L. J. Huo, S. Q. Zhang, X. Guo, F. Xu, Y. F. Li, J. H. Hou, *Angew. Chem. Int. Ed.* 2011, 50, 1.

[7] a) J. Peet, J. Y. Kim, N. E. Coates, W. L. Ma, D. Moses, A. J. Heeger, G. C. Bazan, *Nat. Mater.* 2007, 6, 497; b) J. H. Hou, H. Y. Chen, S. Q. Zhang, G. Li, Y. Yang, *J. Am. Chem. Soc.* 2008, 130, 16144; c) J. C. Bijleveld, A. Zoombelt, S. G. J. Mathijssen, M. M. Wienk, M. Turbiez, D. M. de Leeuw, R. A. J. Janssen, *J. Am. Chem. Soc.* 2009, 131, 16616; d) C. H. Woo, P. M. Beaujuge, T. W. Holcombe, O. P. Lee, J. M. J. Fréchet, *J. Am. Chem. Soc.* 2010, 132, 15547; e) L. Huo, J. Hou, H.-Y. Chen, S. Zhang, Y. Jiang, T. Chen, Y. Yang, *Macromolecules* 2009, 42, 6564; f) E. J. Zhou, Q. S. Wei, S. Yamakawa, Y. Zhang, K. Tajima, C. H. Yang, K. Hashimoto, *Macromolecules* 2010, 43, 821; g) W. W. Li, W. S. C. Roelofs, M. M. Wienk, R. A. J. Janssen, *J. Am. Chem. Soc.* 2012, 134, 13787.

[8] L. T. Dou, J. Gao, E. Richard, J. B. You, C.-C. Chen, K. C. Cha, Y. J. He, G. Li, Y. Yang, *J. Am. Chem. Soc.* 2012, 134, 10071.

[9] a) A. J. Kronemeijier, E. Gili, M. Shahid, J. Pivnay, A. Salleo, M. Heeney, H. Sirringhaus, *Adv. Mater.* 2012, 24, 1558; b) J. S. Ha, K. H. Kim, D. H. Choi, *J. Am. Chem. Soc.* 2011, 133, 10364; c) M. Shahid, T. Mccarthy-Ward, J. Labram, S. Rossbauer, E. B. Domingo, S. E. Watkins, N. Stingelin, T. D. Anthopoulos, M. Heeney, *Chem. Sci.* 2012, 3, 181.

[10] a) M. Shahid, R. S. Ashraf. Z. G. Huang, A. J. Kronemeijier, T. Mccarthy-Ward, I. McCulloch, J. R. Durrant, H. Sirringhaus, M. Heeney, *J. Mater. Chem.* 2012, 22, 12817; b) A. M. Ballantyne, L. C. Chen, J. Nelson, D. D. C. Bradley, Y. Astuti, A. Maurano, C. G. Shuttle, J. R. Durrant, M. Heeney, W. Duffy, I. Mcculloch, *Adv. Mater.* 2007, 19, 4544; c) M. F. G. Klein, M. Pfaff, E. Muller, J. Czolk, M. Reinhard, S. Valouch, U. Lemmer, A. Colsmann, D. Gerthsen, *J. Polym. Sci. Part B: Polym. Phys.* 1993, 31, 735.

[11] H. A. Saadeh, L. Y. Lu, F. He, J. E. Bullock, W. Wang, B. Carsten, L. P. Yu. *ACS Macro Lett.* 2012, 1, 361.

[12] G. Li, C.-W. Chu, V. Shrotriya, J. Huang, Y. Yang, *Appl. Phys. Lett.* 2006, 88, 253503.

[13] Y. J. He, H.-Y. Chen, J. H. Hou, Y. F. Li, *J. Am. Chem. Soc.* 2010, 132, 1377.

[14] a) J. Burdick. T. Glatfelter. *Solar Cells* 1986, 18, 301; b) M. Meusel, C. Baur, G. Letay, A. W. Bett, W. Warta, E. Fernandez, *Prog. Photovolt. Res.* 2003, 11, 499.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. A conjugated polymer comprising a repeated unit having the structure of formula (I)

wherein each $R_1$ independently is H, a halogen, optionally substituted alkyl, optionally substituted aryl, or optionally substituted heteroaryl;

each R' independently is H, a halogen, optionally substituted alkyl, optionally substituted aryl, or optionally substituted heteroaryl;

each i, independently, is 0, 1, or 2;

D is a donor moiety; and n is an integer wherein D is selected from the group consisting of:
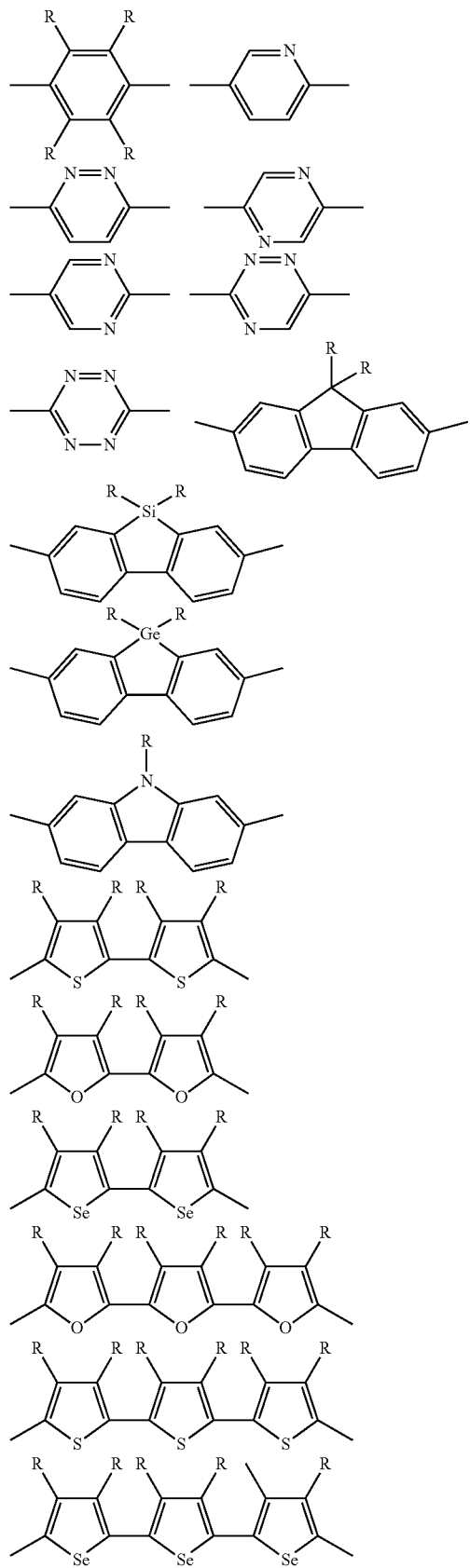
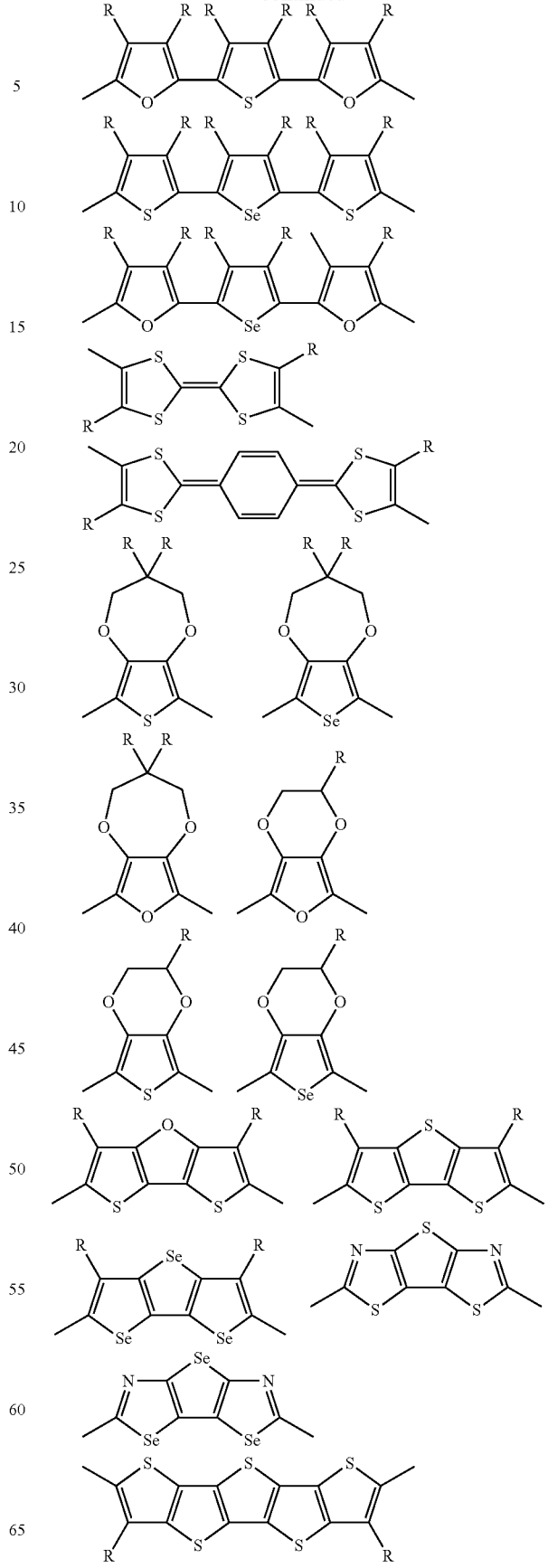

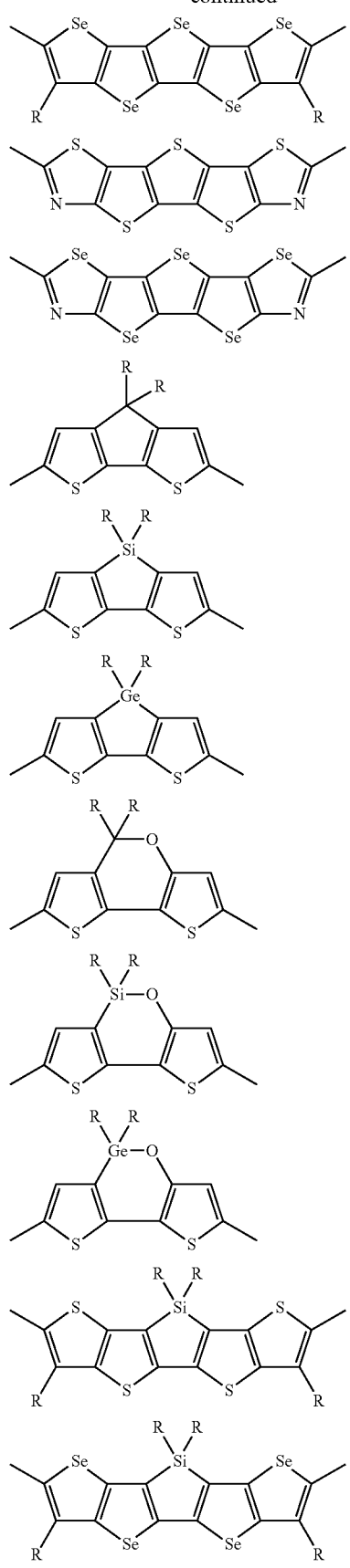
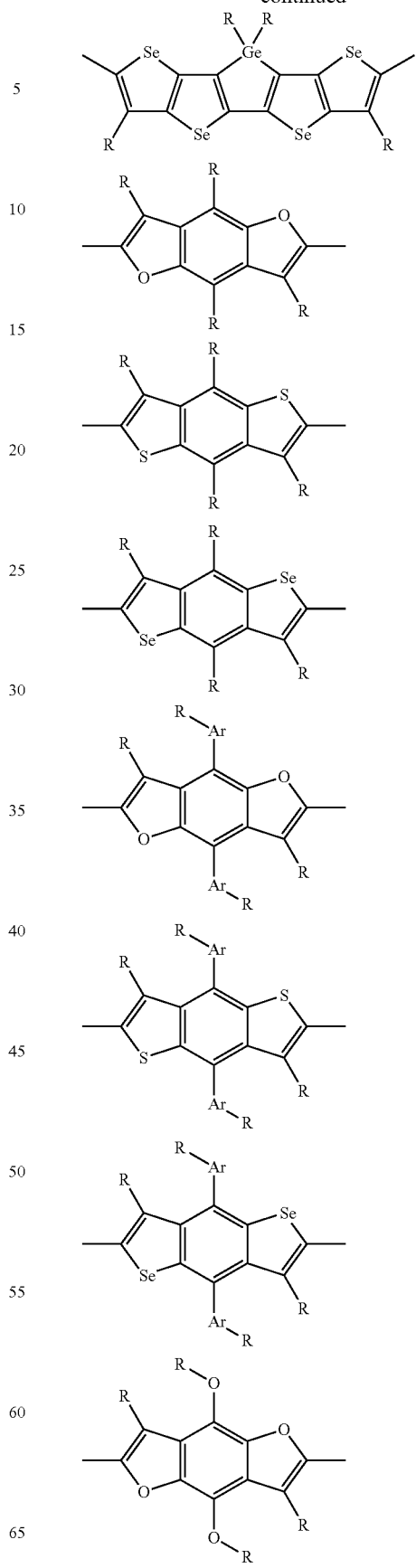

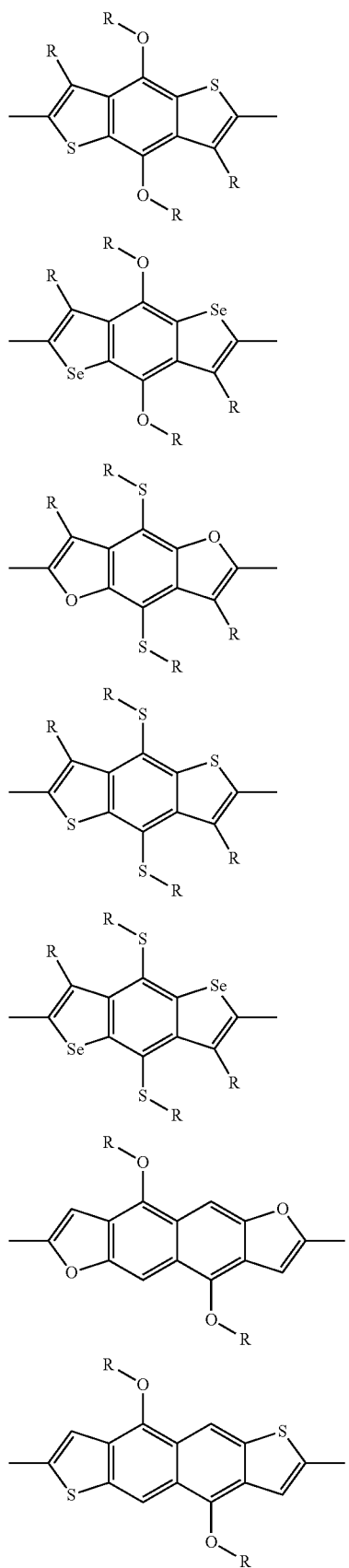
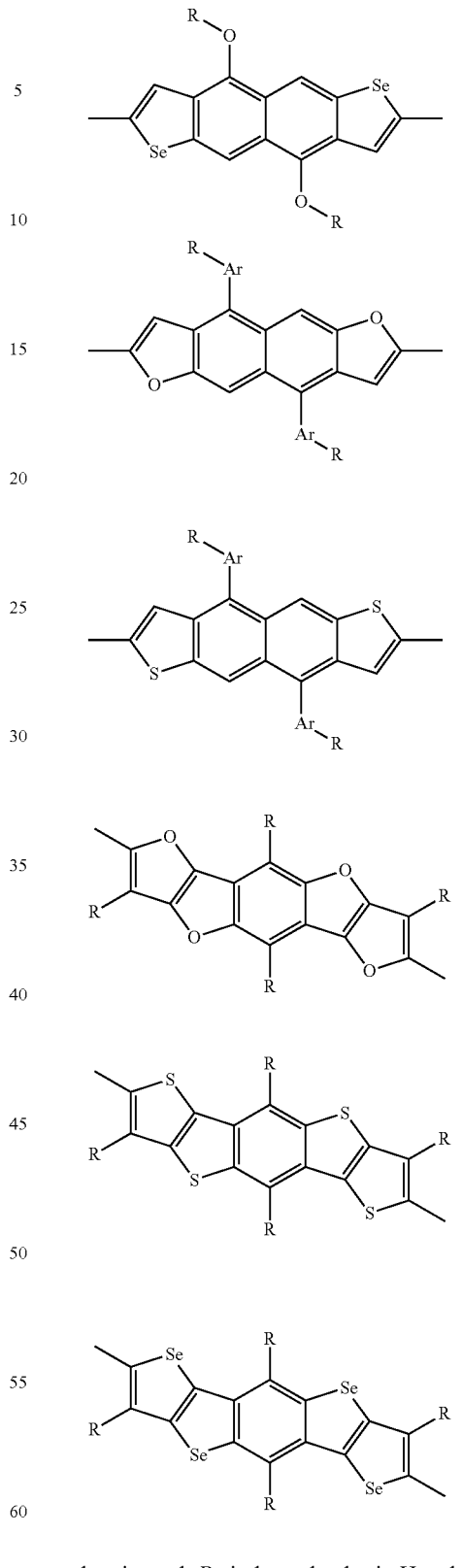
wherein each R, independently, is H, a halogen, cyano, nitro, optionally substituted alkyl, optionally substituted aryl, or optionally substituted heteroaryl; and
each Ar, independently, is optionally substituted arylene, or optionally substituted heteroarylene.

2. The conjugated polymer of claim 1, wherein D is selected from the group consisting of:
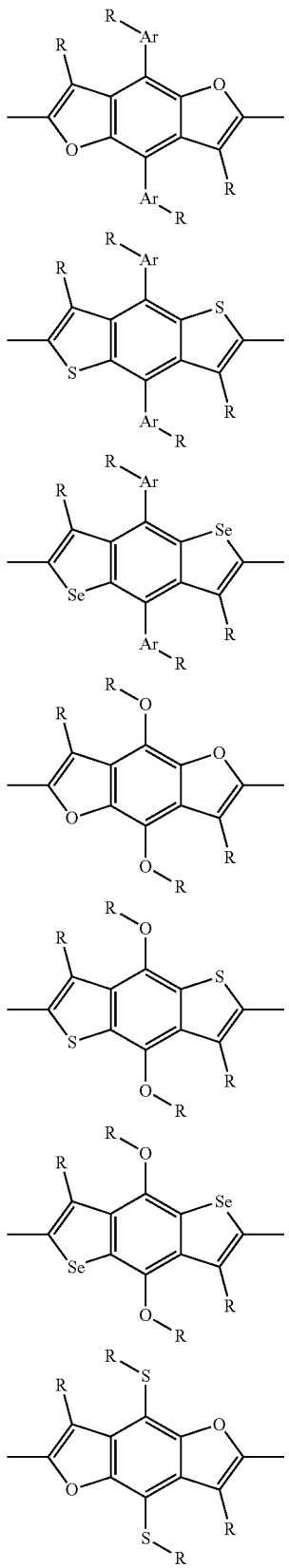
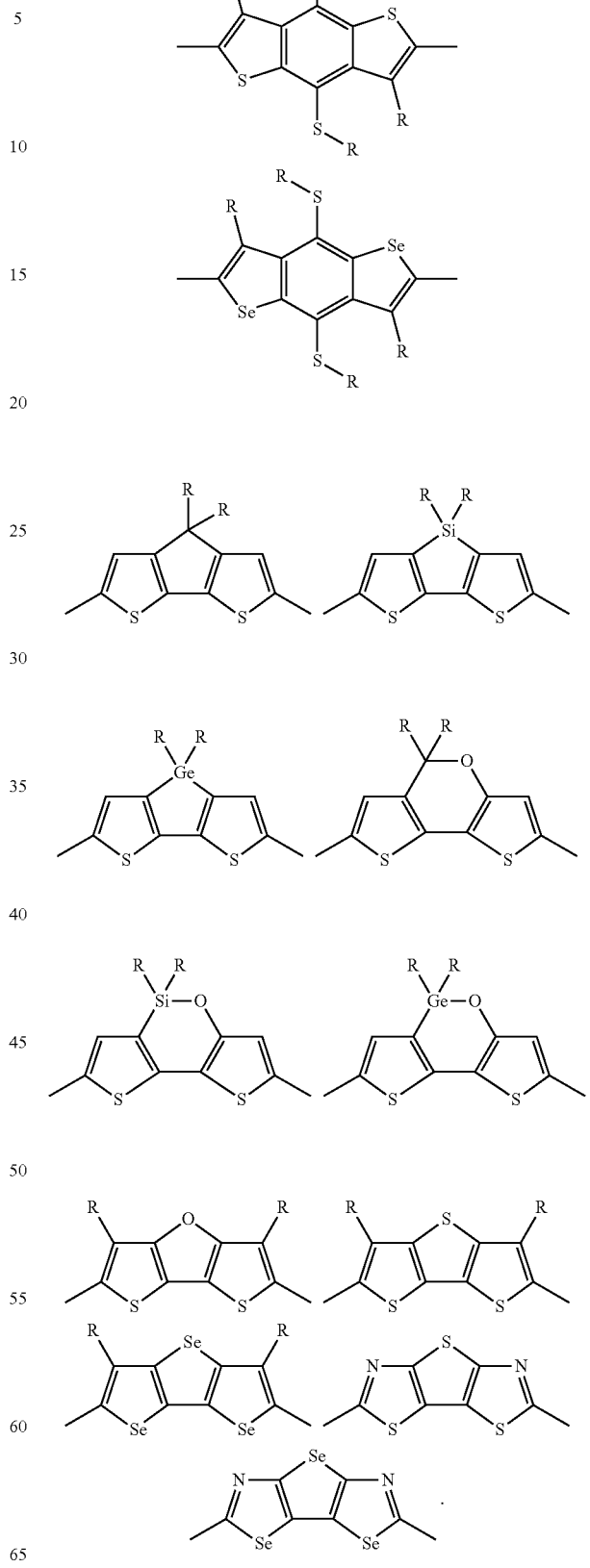

3. The conjugated polymer of claim 1, wherein D is selected from the group consisting of:

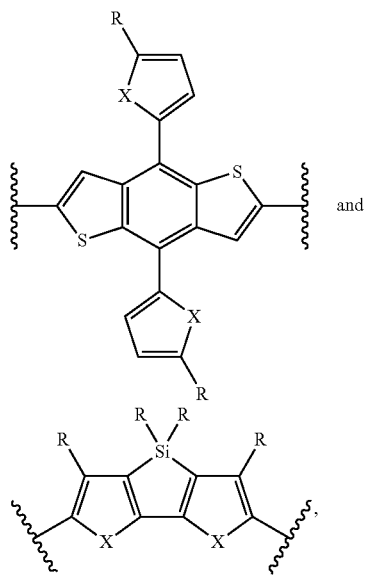

and wherein x is S and R is an alkyl group with carbon atom number of 1-18.

4. The conjugated polymer of claim 1, wherein the repeated unit has the structure of formula (IV) or (V)

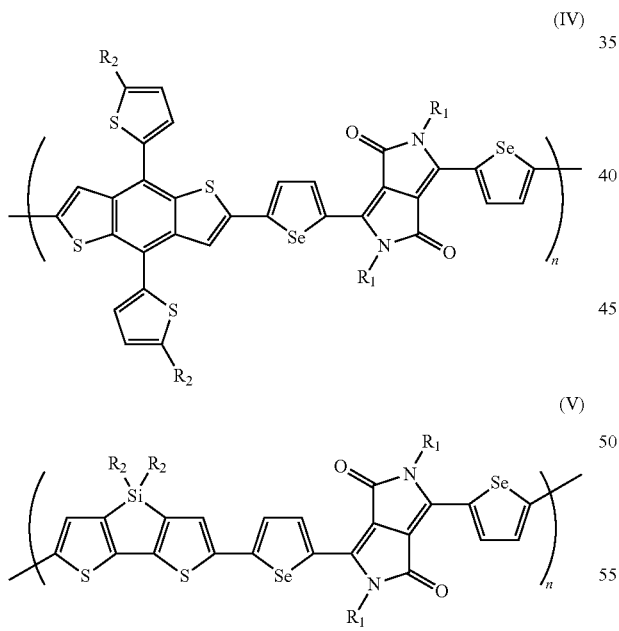

wherein each $R_1$ and each $R_2$ is independently optionally substituted alkyl or optionally substituted aryl.

5. The conjugated polymer of claim 4, wherein each $R_1$ and each $R_2$ is independently selected from $C_4$-$C_{12}$ alkyl.

6. The conjugated polymer of claim 5, wherein $R_1$ is 2-butyloctyl and $R_2$ is ethylhexyl.

7. A photovoltaic device comprising a conjugated polymer of claim 1 as a photovoltaic material.

8. The photovoltaic device of claim 7, wherein the photovoltaic device is a single junction polymer solar cell, a tandem polymer solar cell, a visibly-transparent solar cell, or a photo-detector.

9. The photovoltaic device of claim 8, wherein the photovoltaic device has a bulk heterojunction structure.

10. The photovoltaic device of claim 9, wherein the bulk heterojunction structure includes a polymer of claim 1, and a fullerene.

11. The photovoltaic device of claim 10, where the fullerene is [6,6]-phenyl $C_{61}$ butyric acid methyl ester or [6,6]-phenyl $C_{71}$ butyric acid methyl ester.

12. A method of making a conjugated polymer of claim 1, comprising co-polymerizing a monomer having the structure of formula (II) and a monomer having the structure of formula (III):

$$X-D-X \qquad (II)$$

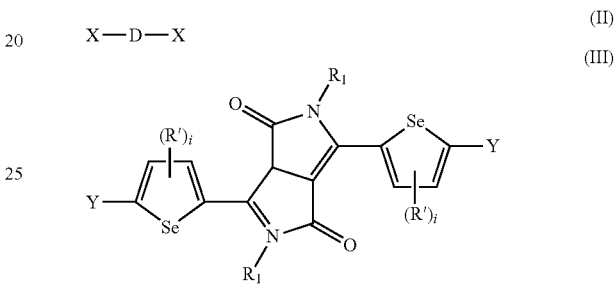

wherein each X, independently, is a boronic acid group, a boronic acid ester group, a magnesium halide group, a zinc halide group, or a trialkyl tin group; and each Y, independently, is Cl, Br, I; or
each X, independently, is Cl, Br, or I; and each Y, independently, is a boronic acid group, a boronic acid ester group, a magnesium halide group, a zinc halide group, or a trialkyl tin group.

13. A compound having the structure of formula (III):

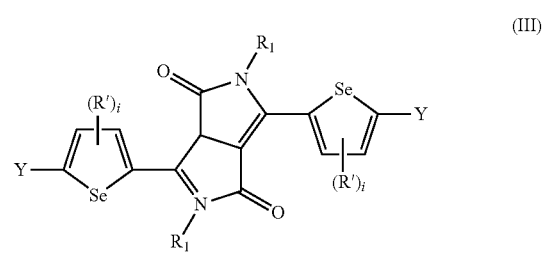

wherein each $R_1$ independently is H, a halogen, optionally substituted alkyl, optionally substituted aryl, or optionally substituted heteroaryl, wherein each $R_1$ is independently selected from $C_4$-$C_{12}$ alkyl;
each R' independently is H, a halogen, optionally substituted alkyl, optionally substituted aryl, or optionally substituted heteroaryl;
each i, independently, is 0, 1, or 2; and
each Y, independently, is a boronic acid group, a boronic acid ester group, a magnesium halide group, a zinc halide group, a trialkyl tin group, Cl, Br, or I.

14. The compound of claim 13, wherein $R_1$ is 2-butyloctyl.

15. The compound of claim 13, wherein each Y is Cl, Br, or I.

16. The conjugated polymer of claim 4, wherein the repeated unit has the structure of
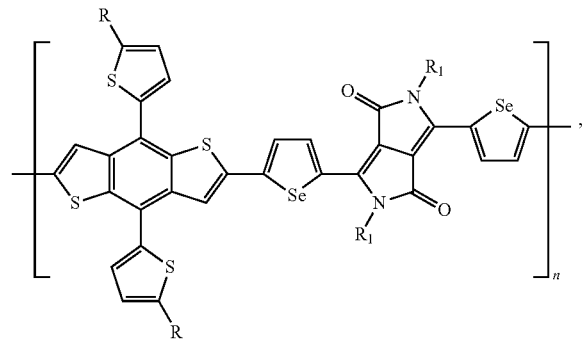
wherein R=2-ethylhexyl, $R_1$=2-butyloctyl.
17. The conjugated polymer of claim 4, wherein the repeated unit has the structure of
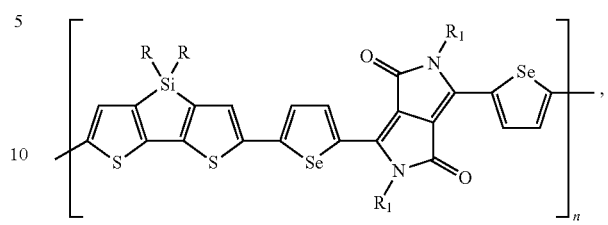
wherein R=2-ethylhexyl, $R_1$=2-butyloctyl.
* * * * *